(12) United States Patent
Burns et al.

(10) Patent No.: US 8,084,456 B2
(45) Date of Patent: *Dec. 27, 2011

(54) PYRAZINE-BASED TUBULIN INHIBITORS

(75) Inventors: Christopher John Burns, Seddon (AU);
Andrew Frederick Wilks, South Yarra (AU); Xianyong Bu, Viewbank (AU);
Harrison Sikanyika, Kilsyth (AU);
Michael Francis Harte, Viewbank (AU)

(73) Assignee: YM Biosciences Australia Pty Ltd, Melbourne, Victoria (AU)

( * ) Notice: Subject to any disclaimer, the term of this patent is extended or adjusted under 35 U.S.C. 154(b) by 989 days.

This patent is subject to a terminal disclaimer.

(21) Appl. No.: 10/538,499

(22) PCT Filed: Dec. 11, 2003

(86) PCT No.: PCT/AU03/01661
§ 371 (c)(1),
(2), (4) Date: Aug. 3, 2006

(87) PCT Pub. No.: WO2004/052868
PCT Pub. Date: Jun. 24, 2004

(65) Prior Publication Data
US 2007/0082894 A1    Apr. 12, 2007

Related U.S. Application Data

(60) Provisional application No. 60/483,399, filed on Jun. 26, 2003.

(30) Foreign Application Priority Data

Dec. 11, 2002  (AU) ................. 2002953255

(51) Int. Cl.
*A61K 31/4965* (2006.01)
(52) U.S. Cl. ................. 514/255.06; 544/336; 546/268.1
(58) Field of Classification Search ............. 514/255.06; 544/336; 546/268.1
See application file for complete search history.

(56) References Cited

U.S. PATENT DOCUMENTS 7,122,550 B2 * 10/2006 Burns et al. ............. 514/255.05

FOREIGN PATENT DOCUMENTS

| WO | WO-02/060492 | 8/2002 |
| WO | WO-03/031406 | 4/2003 |
| WO | WO-03/099796 | 12/2003 |
| WO | WO-2004/000318 | 12/2003 |
| WO | WO-2004/085409 | 10/2004 |
| WO | WO-2005/054199 | 6/2005 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, 18.*
Chawla, et al. Curr. Res. & Info. Pharm. Sci. (CRIPS), 5, 1, 2004, 9-12.*
Supplementary European Search Report for EP 03778161, search completed Jul. 10, 2007, 2 pages.
Zimmermann et al., Archie der Pharmazie (1996) 329(7):371-376.
Ding et al., J. Am. Chem. Soc. (2002) 124(8):1594-1596.
International Search Report for PCT/AU2003/001661, mailed on Mar. 11, 2004, 2 pages.

* cited by examiner

*Primary Examiner* — James O Wilson
*Assistant Examiner* — Douglas M Willis
(74) *Attorney, Agent, or Firm* — Morrison & Foerster LLP

(57) ABSTRACT

A compound of general formula (I) or pharmaceutically acceptable prodrugs, salts, hydrates, solvates, crystal forms or diastereomers thereof is described. A method of treating a hyperproliferation-related disease state or disorder in a subject using a compound of formula (I) is also described.

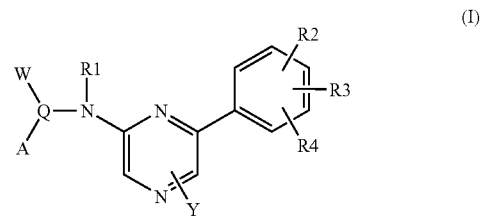

15 Claims, No Drawings

PYRAZINE-BASED TUBULIN INHIBITORS

CROSS-REFERENCE TO RELATED APPLICATIONS

This application is the national phase of PCT application PCT/AU2003/001661 having an international filing date of 11 Dec. 2003, which claims priority from Australian application 2002953255, filed 11 Dec. 2002, and U.S. provisional application 60/483,399, filed 26 Jun. 2003. The contents of these documents are incorporated herein by reference.

FIELD OF THE INVENTION

The present invention involves compounds represented by Formula (I) herein below, pharmaceutical compositions comprising such compounds and methods of suppressing the growth of cancers and other proliferative diseases using such compounds.

BACKGROUND OF THE INVENTION

There are many human and veterinary diseases that stem from processes of uncontrolled or abnormal cellular proliferation. Most important among these diseases is cancer, the generic name given to a broad range of cellular malignancies characterized by unregulated growth and lack of differentiation. Psoriasis is another disease that is characterized by uncontrolled or abnormal cellular proliferation. Psoriasis is a common chronic skin disease characterized by the presence of dry scales and plaques. The disease results from hyperproliferation of the epidermis and incomplete differentiation of keratinocytes. Psoriasis often involves the scalp, elbows, knees, back, buttocks, nails, eyebrows, and genital regions, and may range in severity from mild to extremely debilitating, resulting in psoriatic arthritis, pustular psoriasis, and exfoliative psoriatic dermatitis. There is, at present, no general therapeutic cure that exists for psoriasis. Whilst milder cases are often treated with topical corticosteroids, more severe cases may be treated with antiproliferative agents, such as the antimetabolite methotrexate, the DNA synthesis inhibitor hydroxyurea, and the microtubule disrupter colchicine.

Other diseases associated with an abnormally high level of cellular proliferation include restenosis, where vascular smooth muscle cells are involved; inflammatory disease states, where endothelial cells, inflammatory cells and glomerular cells are involved; myocardial infarction, where heart muscle cells are involved; glomerular nephritis, where kidney cells are involved; transplant rejection, where endothelial cells are involved; and infectious diseases such as HIV infection and malaria, where certain immune cells and/or other infected cells are involved.

Inhibition of cellular proliferation can be brought about by several mechanisms, including; alkylating agents; topoisomerase inhibitors; nucleotide analogues; antibiotics; hormone antagonists; and nucleic acid damaging agents; inter alia. One pharmacologically important mechanism of inhibiting cellular proliferation is by means of binding tubulin. Tubulin is an asymmetric dimer composed of alpha and beta subunits, that polymerizes to form structural components of the cytoskeleton called microtubules. Microtubules must be highly dynamic in order to carry out many of their functions. At certain stages of the cell cycle, or in particular cell types or organelles, stable microtubules are required, such as for transport within axons or for ciliary and flagellar movement. Micro-tubules assemble during the G2 phase of the cell cycle, and participate in the formation of the mitotic spindle which facilitates the segregation of sister chromatids during the process of cell division. The essential role of microtubules in cell division and the ability of drugs that interact with tubulin to interfere with the cell cycle have made tubulin a successful target for applications that include anti-cancer drugs, fungicides, and herbicides. Typical tubulin ligands such as colchicine, paditaxel, the Vinca alkaloids such as vinblastine, the epothilones, the halicondrins, benomyl and mebendazole directly inhibit cell division by binding to tubulin which leads to the arrest of the cell cycle at the G2/M boundary of mitosis. This mechanism is the basis of the therapeutic value of compounds of this type, such as treating gout with colchicine, restenosis with paclitaxel, cancer with paditaxel, vinblastine, epothilones and halichondrins, and fungal infections with benomyl and malaria and helminths with mebendazole.

Interfering with microtubule dynamics or stability can inhibit cell division in several ways. Both stablilizing microtubules or inhibiting their polymerization will prevent the cytoskeleton restructuring that is required at several points in the cell cycle and lead to an arrest of the cell's progression from one stage in the cell cycle to the next. Three main classes of tubulin-binding drugs, namely colchicine analogues, Vinca alkaloids, and the taxanes, have been identified, each of which possesses a specific binding site on the $\beta$-tubulin molecule. Paclitaxel (Taxol™) and related taxanes represent a class of drugs that stabilize microtubules, a process that ultimately leads to the "freezing" of the microtubule structures so that they cannot be restructured (Jordan M A. and Wilson L., 1998). Subsequent arrest at mitosis induces the apoptotic mechanism to cause cell death. A number of colchicine analogues, as well as several other compounds that bind to the same site on $\beta$-tubulin as colchicine disrupt tubulin polymerization and disrupt microtubular formation. Vinblastine and several other vinca-related drugs bind to a site that is distinct from the colchicine site. Compounds that bind at the Vinca-site prevent microtubule formation and destabilize microtubules (Jordan et al, 1986; Rai and Wolff (1996). This invention is therefore directed to compounds that potentially modulate microtubule dynamics by binding to tubulin.

Accordingly, the present invention aims to provide compounds which are directly or indirectly toxic to actively dividing cells and are useful in the treatment of cancer, viral and bacterial infections, vascular restenosis, inflammatory diseases, autoimmune diseases, or psoriasis. The present invention is also directed to therapeutic compositions for treating said conditions. Further aspects of the invention are to provide methods for killing actively proliferating cells, such as cancerous, bacterial, or epithelial cells, and treating all types of cancers, infections, inflammatory, and generally proliferative conditions. A further aspect relates to provide methods for treating other medical conditions characterized by the presence of rapidly proliferating cells, such as psoriasis and other skin disorders.

In one embodiment, the method of the invention is used in the treatment of sarcomas, carcinomas and/or leukemias. Exemplary disorders for which the subject method can be used alone or as part of a treatment regimen include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In certain embodiments, the method of the invention is to be used to treat disorders such as carcinomas forming from tissue of the breast, prostate, kidney, bladder or colon.

In other embodiments, the method of the invention is used to treat hyperplastic or neoplastic disorders arising in adipose tissue, such as adipose cell tumors, e.g., lipomas, fibrolipomas, lipoblastomas, lipomatosis, hibemomas, hemangiomas and/or liposarcomas.

In still other embodiments, infectious and parasitic agents (e.g. bacteria, trypanosomes, fungi, etc) can also be controlled using the subject compositions and compounds.

SUMMARY OF THE INVENTION

The present inventors have found that a group of compounds based upon a disubstituted pyrazine scaffold are inhibitors of the growth and proliferation of cancer cells. The present inventors have further shown that these compounds can bind to tubulin. Such compounds would also be useful in the treatment of other hyperproliferation related disorders and further may be useful in the treatment of tyrosine kinase-based disorders.

Accordingly, in a first aspect the present invention provides a compound of the general formula

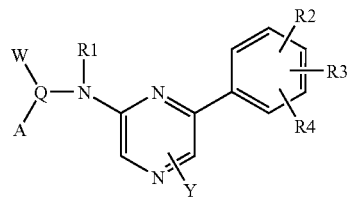

I or pharmaceutically acceptable prodrugs, salts, hydrates, solvates, crystal forms or diastereomers thereof, wherein:
R1 is H, $C_{1-6}$alkyl, $C_{1-6}$alkylNR5R6, $C_{1-6}$alkylNR5COR6, $C_{1-6}$alkylNR5SO$_2$R6, $C_{1-6}$alkylCO$_2$R5, $C_{1-6}$alkylCONR5R6, where R5 and R6 are each independently H, $C_{1-4}$alkyl, aryl, hetaryl, $C_{1-4}$alkylaryl, $C_{1-4}$alkylhetaryl or may be joined to form an optionally substituted 3-8 membered ring optionally containing an atom selected from O, S, NR7 and R7 is selected from H, $C_{1-4}$alkyl;
R2, R3 and R4 are each independently H, halogen, $C_{1-4}$alkyl, OH, OC$_{1-4}$alkyl, CF$_3$, OCF$_3$, CN, $C_{1-4}$alkylNR8R9, OC$_{1-4}$alkylNR8R9, OCONR8R9, NR8R9, NR8COR9, NR10CONR8R9, NR8SO$_2$R9, COOR8, CONR8R9; and R8, R9 are each independently H, $C_{1-4}$ alkyl, $C_{1-4}$ alkyl cycloalkyl, or may be joined to form an optionally substituted 3-8 membered ring optionally containing an atom selected from O, S, NR11; R10 and R11 are independently selected from H, $C_{1-4}$ alkyl, CF$_3$;
alternatively, two of R2, R3 and R4, when located on adjacent carbon atoms, may be joined to form a ring system selected from:

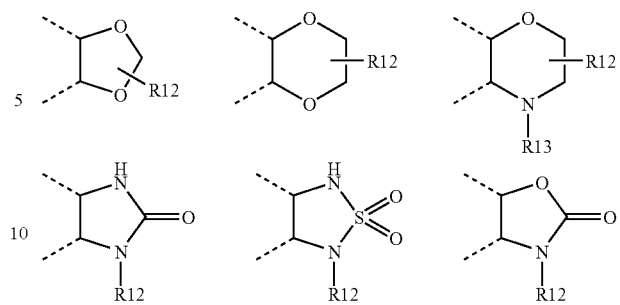

where R12 is selected from H. $C_{1-4}$ alkyl, CF$_3$ and R13 is selected from H, $C_{1-4}$ alkyl, CF$_3$, COR14, SO$_2$R14; and R14 is selected from H, $C_{1-4}$ alkyl;
Q is a bond, or $C_{1-4}$ alkyl;
W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, OC$_{1-4}$alkyl, NR15R16; and R15, and R16 are each independently H, $C_{1-4}$ alkyl, $C_{1-4}$ alkyl cycloalkyl, $C_{1-4}$ alkyl cyclohetalkyl, aryl, hetaryl, or may be joined to form an optionally substituted 3-8 membered ring optionally containing an atom selected from O,S, NR17 and R17 is selected from H, $C_{1-4}$ alkyl;
A is aryl, hetaryl optionally substituted with 0-3 substituents independently chosen from halogen, $C_{1-4}$ alkyl, CF$_3$, aryl, hetaryl, OCF$_3$, OC$_{1-4}$alkyl, OC$_{2-5}$alkylNR18R19, Oaryl, Ohetaryl, CO$_2$R18, CONR18R19, NR18R19, $C_{1-4}$ alkylNR18R19, NR20C$_{1-4}$alkylNR18R19, NR18COR19, NR20CONR18R19, NR18SO$_2$R19; and R18, R19 are each independently H, $C_{1-4}$ alkyl, $C_{1-4}$ alkyl cyclohetalkyl, aryl, hetaryl, $C_{1-4}$alkyl aryl, $C_{1-4}$ alkyl hetaryl, or may be joined to form an optionally substituted 3-8 membered ring optionally containing an atom selected from O, S, NR21; and R20 is selected from H, $C_{1-4}$ alkyl; and R21 is selected from H, $C_{1-4}$ alkyl; and
Y is selected from H, $C_{1-4}$alkyl, OH, NR22R23, and R22, and R23 are each independently H, $C_{1-4}$ alkyl.

In a second aspect the present invention provides a composition comprising a carrier and at least one compound of the first aspect of the invention.

In a third aspect the present invention provides a method of treating a hyperproliferation-related disease state or disorder in a subject, the method comprising administering a therapeutically effective amount of at least one compound of the first aspect or a therapeutically effective amount of a composition of the second aspect.

In a fourth aspect the present invention provides a method of treating a tyrosine kinase-associated disease state or disorder in a subject, the method comprising administering a therapeutically effective amount of at least one compound of the first aspect of the invention or a therapeutically effective amount of a composition of the second aspect of the invention.

In a fifth aspect, the present invention provides a method of modulating microtubule polymerisation in a cell by the administration of a compound according to the first aspect.

DETAILED DESCRIPTION OF THE INVENTION

In a first aspect the present invention provides a compound of the general formula

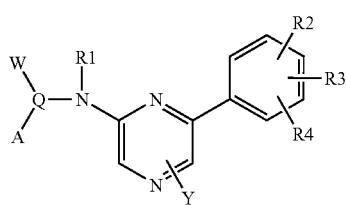

or pharmaceutically acceptable prodrugs, salts, hydrates, solvates, crystal forms or diastereomers thereof, wherein:

R1 is H, $C_{1-6}$alkyl, $C_{1-6}$ alkylNR5R6, $C_{1-4}$alkylNR5COR6, $C_{1-6}$alkylNR5SO$_2$R6, $C_{1-6}$alkylCO$_2$R5, $C_{1-6}$alkylCONR5R6, where R5 and R6 are each independently H, $C_{1-4}$alkyl, aryl, hetaryl, $C_{1-4}$alkylaryl, $C_{1-4}$alkylhetaryl or may be joined to form an optionally substituted 3-8 membered ring optionally containing an atom selected from O, S, NR7 and R7 is selected from H, $C_{1-4}$ alkyl;

R2, R3 and R4 are each independently H, halogen, $C_{1-4}$alkyl, OH, OC$_{1-4}$alkyl, CF$_3$, OCF$_3$, CN, $C_{1-4}$alkylNR8R9, OC$_{1-4}$alkylNR8R9, OCONR8R9, NR8R9, NR8COR9, NR10CONR8R9, NR8SO$_2$R9, COOR8, CONR8R9; and R8, R9 are each independently H, $C_{1-4}$ alkyl, $C_{1-4}$ alkyl cycloalkyl, or may be joined to form an optionally substituted 3-8 membered ring optionally containing an atom selected from O, S, NR11; R10 and R11 are independently selected from H, $C_{1-4}$ alkyl, CF$_3$;

Alternatively, two of R2, R3 and R4, when located on adjacent carbon atoms, may be joined to form a ring system selected from:

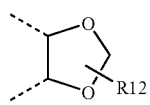 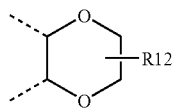 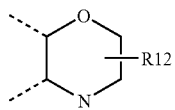

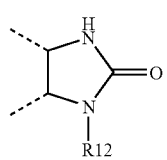 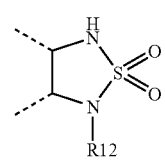 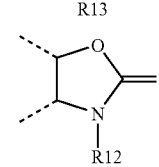

where R12 is selected from H, $C_{1-4}$ alkyl, CF$_3$ and R13 is selected from H, $C_{1-4}$ alkyl, CF$_3$, COR14, SO$_2$R14; and R14 is selected from H, $C_{1-4}$ alkyl;

Q is a bond, or $C_{1-4}$ alkyl;

W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, OC$_{1-4}$alkyl, NR15R16; and R15, and R16 are each independently H, $C_{1-4}$ alkyl, $C_{1-4}$ alkyl cycloalkyl, $C_{1-4}$ alkyl cyclohetalkyl, aryl, hetaryl, or may be joined to form an optionally substituted 3-8 membered ring optionally containing an atom selected from O, S, NR17 and R17 is selected from H, $C_{1-4}$ alkyl;

A is aryl, hetaryl optionally substituted with 0-3 substituents independently chosen from halogen, $C_{1-4}$ alkyl, CF$_3$, aryl, hetaryl, OCF$_3$, OC$_{1-4}$alkyl, OC$_{2-5}$alkylNR18R19, Oaryl, Ohetaryl, CO$_2$R18, CONR18R19, NR18R19, $C_{1-4}$ alkylNR18R19, NR20C$_{1-4}$alkylNR18R19, NR18COR19, NR20CONR18R19, NR18SO$_2$R19; and R18, R19 are each independently H, $C_{1-4}$ alkyl, $C_{1-4}$ alkyl cyclohetalkyl, aryl, hetaryl, $C_{1-4}$alkyl aryl, $C_{1-4}$ alkyl hetaryl, or may be joined to form an optionally substituted 3-8 membered ring optionally containing an atom selected from O, S, NR21; and R20 is selected from H, $C_{1-4}$ alkyl; and R21 is selected from H, $C_{1-4}$ alkyl;

Y is selected from H, $C_{1-4}$alkyl, OH, NR22R23, and R22, and R23 are each independently H, $C_{1-4}$ alkyl.

In the above description it will be appreciated that:

$C_{1-4}$ alkyl means an unsubstituted or optionally substituted straight or branched alkyl chain Aryl means unsubstituted or optionally substituted phenyl or naphthyl.

Hetaryl means an unsubstituted or optionally substituted 5- or 6-membered heteroaromatic ring containing one or more heteroatoms selected from O, N, S.

Cycloalkyl means a 3-8 membered saturated ring

Cyclohetalkyl means a 3-8 membered saturated ring containing 1-3 heteroatoms selected from O, S, NR18, where R18 is H, $C_{1-4}$ alkyl, aryl, hetaryl.

In a preferred embodiment, the compound is selected from the compounds set out in Table 1.

In a further preferred embodiment the compound is selected from a compound of the general formula II

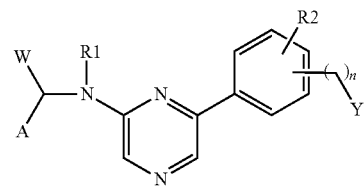

or pharmaceutically acceptable prodrugs, salts, hydrates, solvates, crystal forms or diastereomers thereof, wherein:

R1 is H, $C_{1-6}$alkyl, $C_{1-6}$ alkylNR3R4, where R3 and R4 are each independently H, $C_{1-4}$alkyl, or may be joined to form an optionally substituted 3-8 membered ring optionally containing an atom selected from O, S, NR5 and R5 is selected from H, $C_{1-4}$ alkyl;

A is aryl, hetaryl optionally substituted with 0-3 substituents independently chosen from halogen, $C_{1-4}$ alkyl, CF$_3$, aryl, hetaryl, OCF$_3$, OC$_{1-4}$alkyl, OC$_{2-5}$alkylNR6R7, Oaryl, Ohetaryl, CO$_2$R6, CONR6R7, NR6R7, $C_{1-4}$ alkylNR6R7, NR8C$_{1-4}$alkylNR6R7, NR6COR7, NR8CONR6R7, NR6SO$_2$R7; and R6, R7 are each independently H, $C_{1-4}$ alkyl, $C_{1-4}$ alkyl cyclohetalkyl, aryl, hetaryl, $C_{1-4}$alkyl aryl, $C_{1-4}$ alkyl hetaryl, or may be joined to form an optionally substituted 3-8 membered ring optionally containing an atom selected from O, S, NR9; and R8 is selected from H, $C_{1-4}$ alkyl; and R9 is selected from H, $C_{1-4}$ alkyl;

R2 is 0-2 substituents independently selected from halogen, $C_{1-4}$alkyl, OH, OC$_{1-4}$alkyl, CF$_3$, OCF$_3$, CN, $C_{1-4}$alkylNR10R11, OC$_{1-4}$alkylNR10R11, CO$_2$R10, CONR10R11, NR10R11, NR10COR11, NR12CONR10R11, NR10SO$_2$R11; and R10, R11 are each independently H, $C_{1-4}$ alkyl; and R12 is selected from H, $C_{1-4}$ alkyl;

Y is H, OH, NR12R13; and R12, and R13 are each independently H, $C_{1-4}$ alkyl, or may be joined to form an optionally substituted 3-6 membered ring optionally containing an atom selected from O, S, NR14 and R14 is selected from H, C$_{1-4}$ alkyl; n=0-4;

W is selected from H, C$_{1-4}$alkyl, C$_{2-6}$alkenyl; where C$_{1-4}$alkyl or C$_{2-6}$alkenyl may be optionally substituted with C$_{1-4}$alkyl, OH, OC$_{1-4}$alkyl, NR15R16; and R15, and R16 are each independently H, C$_{1-4}$ alkyl, C$_{1-4}$ alkyl cyclohetalkyl, or may be joined to form an optionally substituted 3-8 membered ring optionally containing an atom selected from O, S, NR17 and R17 is selected from H, C$_{1-4}$ alkyl.

In the above description it will be appreciated that:

C$_{1-4}$ alkyl means an unsubstituted or optionally substituted straight or branched alkyl chain Aryl means unsubstituted or optionally substituted phenyl or naphthyl.

Hetaryl means an unsubstituted or optionally substituted 5- or 6-membered heteroaromatic ring containing one or more heteroatoms selected from O, N, S.

Cycloalkyl means a 3-8 membered saturated ring

Cyclohetalkyl means a 3-8 membered saturated ring containing 1-3 heteroatoms selected from O, S, NR18, where R18 is H, C$_{1-4}$ alkyl, aryl, hetaryl.

In a preferred embodiment R1 is H.

In a further preferred embodiment the compound is selected from the group consisting of:

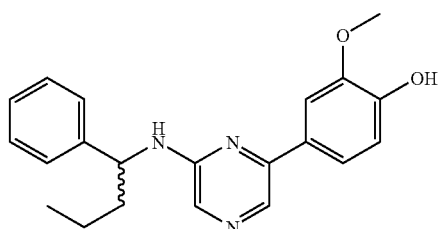

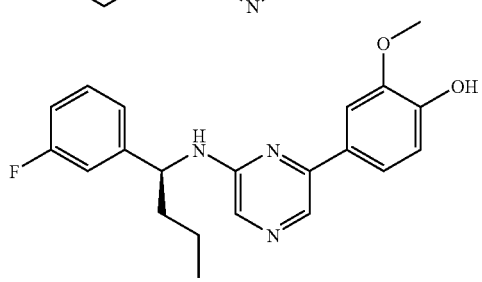

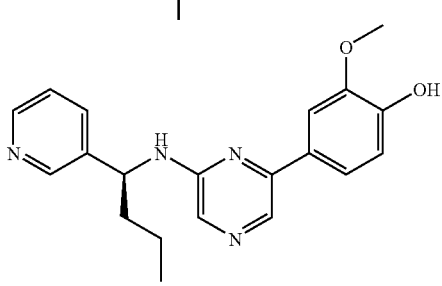

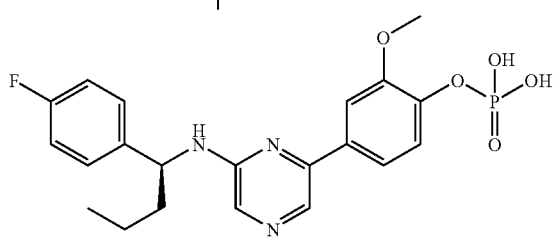

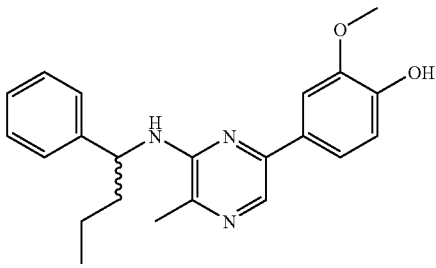

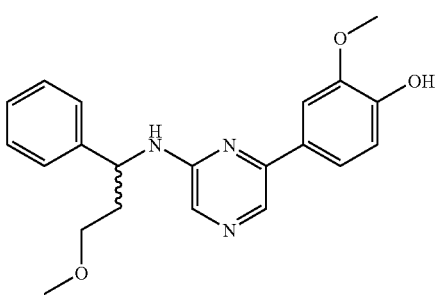

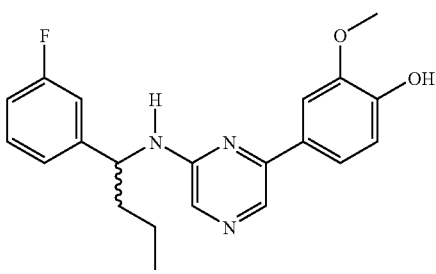

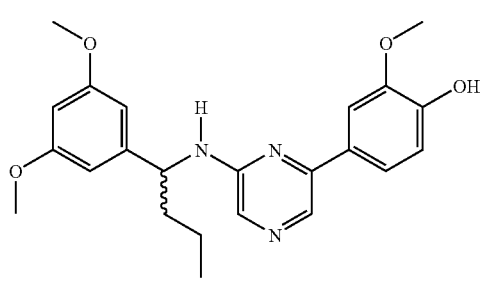

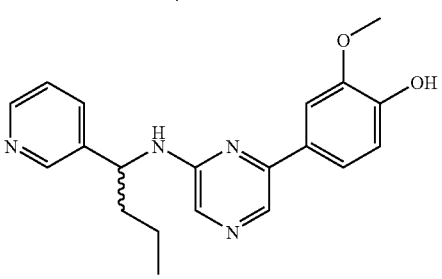

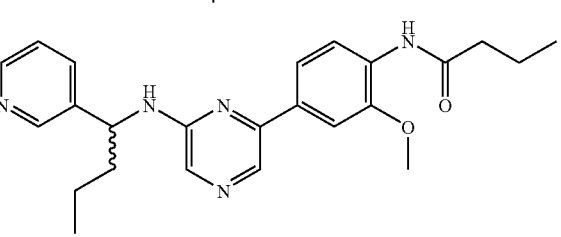

-continued

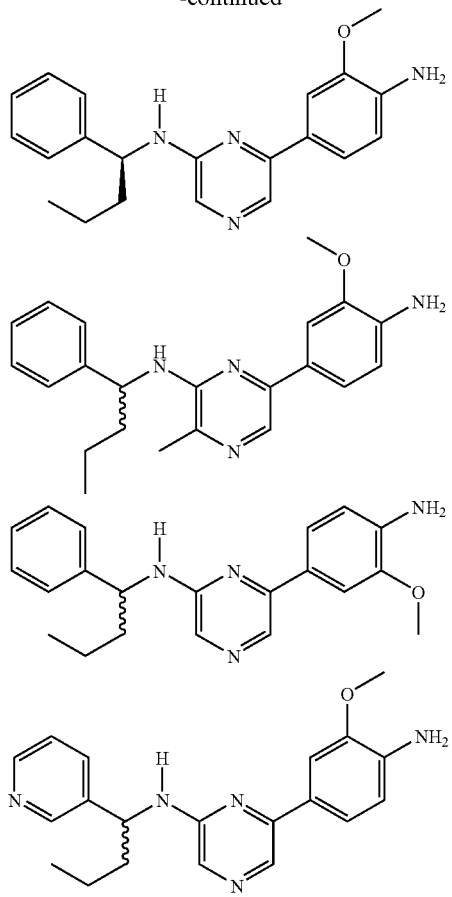

The compounds of this invention include all conformational isomers (eg. cis and trans isomers). The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. The compounds of formula I may also exist as tautomers. This invention relates to the use of all such tautomers and mixtures thereof.

Compounds of formula I having free amino, amido, hydroxy or carboxylic groups can be converted into prodrugs. Prodrugs include compounds wherein an amino acid residue, or a polypeptide chain of two or more (eg, two, three or four) amino acid residues which are covalently joined through peptide bonds to free amino, hydroxy and carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvaline, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain. Prodrugs also include phosphate derivatives of compounds of formula I (such as acids, salts of acids, or esters) joined through a phosphorus-oxygen bond to a free hydroxyl of compounds of formula I. Prodrugs also include compounds wherein acyloxyalkyl or phosphonooxyalkyl moieties are covalently attached to compounds of formula I possessing a free hydroxyl group. Acyloxyalkyl or phosphonooxyalkyl moieties may also be covalently attached to compounds of formula I possessing a pyridyl ring through formation of a N-(acyloxyalkyl)- or N-(phosphonooxyalkyl)-pyridinium salt. This invention also encompasses pharmaceutical compositions containing prodrugs of compounds of the formula I.

In a still further preferred embodiment the compound possesses S chirality at the chiral carbon bearing W, where W is $C_{1-4}$ alkyl or $C_{1-4}$alkylalkoxy. The compound can be used as a purified isomer or as a mixture of any ratio of isomers. It is however preferred that the mixture comprises at least 70%, 80%, 90%, 95%, or 99% of the preferred isomer.

In a second aspect the present invention provides a composition comprising a carrier and at least one compound of the first aspect of the invention.

In a third aspect the present invention provides a method of treating a hyperproliferation-related disease state or disorder in a subject, the method comprising administering a therapeutically effective amount of at least one compound of the first aspect or a therapeutically effective amount of a composition of the second aspect.

As used herein, the term hyperproliferation-related disease state or disorder refers to those disease state or disorders which result from aberrant cellular proliferation.

Preferably, the hyperproliferation-related disease state or disorder is treatable by the modulation of microtubule polymerisation. It has been shown by the present inventors that the compounds of Formula I are capable of binding to tubulin and hence may be used to modulate microtubule polymerisation.

In a preferred embodiment of the present invention the disease state is selected from the group consisting of Atopy, such as Allergic Asthma, Atopic Dermatitis (Eczema), and Allergic Rhinitis; Cell Mediated Hypersensitivity, such as Allergic Contact Dermatitis and Hypersensitivity Pneumonitis; Rheumatic Diseases, such as Systemic Lupus Erythematosus (SLE), Rheumatoid Arthritis, Juvenile Arthritis, Sjögren's Syndrome, Scleroderma, Polymyositis, Ankylosing Spondylitis, Psoriatic Arthritis; Other autoimmune diseases such as Type I diabetes, autoimmune thyroid disorders, and Alzheimer's disease; Viral Diseases, such as Epstein Barr Virus (EBV), Hepatitis B, Hepatitis C, HIV, HTLV 1, Varicella-Zoster Virus (VZV), Human Papilloma Virus (HPV); Cancer, such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma, and carcinomas forming from tissue of the breast, prostate, kidney, bladder or colon, and neoplastic disorders arising in adipose tissue, such as adipose cell tumors, e.g., lipomas, fibrolipomas, lipoblastomas, lipomatosis, hibemomas, hemangiomas and/or liposarcomas; infectious diseases such as viral, malarial and bacterial infections; vascular restenosis; inflammatory diseases, such as autoimmune diseases, glomerular nephritis myocardial infarction and psoriasis.

In a fourth aspect the present invention provides a method of treating a tyrosine kinase-associated disease state or disorder in a subject, the method comprising administering a therapeutically effective amount of at least one compound of the first aspect of the invention or a therapeutically effective amount of a composition of the second aspect of the invention.

As used herein the term "tyrosine kinase-associated disease state" refers to those disorders which result from aberrant tyrosine kinase activity and/or which are alleviated by inhibition of one or more of these enzymes.

The present invention provides pharmaceutical compositions comprising at least one of the compounds of the formula I or II capable of treating a hyperproliferation-related disease state or disorder in an amount effective therefore, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I or II may be administered by any suitable means, for example, orally, such as in the form of tablets, capsules, granules or powders; sublingually; buccally; parenterally, such as by subcutaneous, intravenous, intramuscular, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

The subjects treated in the above methods, in whom which cell growth inhibition is desired, are mammals, including, but not limited to, cows, sheep, goats, horses, dogs, cats, guinea pigs, rats or other bovine, ovine, equine, canine, feline, rodent or murine species, and preferably a human being, male or female.

The term "therapeutically effective amount" means the amount of the subject composition that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and phosphatidyl cholines, both natural and synthetic. Methods to form liposomes are known in the art.

The pharmaceutical composition and method of the present invention may further comprise other therapeutically active compounds as noted herein which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Examples of other therapeutic agents include the following:

cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal antiinflammatory drugs (NSAIDs) such as ibuprofen, aspirin, acetaminophen and cyclooxygenase inhibitors such as rofecoxib, steroids such as prednisolone or dexamethasone, gold compounds, antiproliferative agents such as methotrexate, FK506 (tacrolimus, Prograf), mycophenolate mofetil, antineoplastic agents such as azathioprine, VP-16, etoposide, fludarabine, cisplatin, doxorubicin, adriamycin, amsacrine, camptothecin, cytarabine, gemcitabine, vinblastine, vincristine, fluorodeoxyuridine, melphalan and cyclophosphamide, TNF-α inhibitors such as tenidap, anti-TNF antibodies or soluble TNF receptor, and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one of ordinary skill in the art.

The pharmaceutical composition and method of the present invention may further comprise other therapeutically active compounds as noted herein which are known inhibitors or substrates of drug efflux systems or drug detoxification and excretory systems. Such systems include P-glycoprotein, multidrug resistance-associated protein, lung resistance protein and glutathione S-transferase isoenzymes alpha, mu, pi, sigma, theta, zeta and kappa. Co-administration of drugs known to inhibit or reduce the activity of these systems may increase the efficacy of the compounds described in the present invention through increasing the amount of therapeutic agent in the cell. Using this approach, one may be able to achieve therapeutic efficacy with lower dosages, thus reducing the potential for adverse side effects. Examples of inhibitors or substrates for these systems include; verapamil, probenecid, dipyridamole, ethacrynic acid, indomethacin, sulfasalazine, buthionine sulfoximine, cyclosporin A and tamoxifen.

In the treatment or prevention of hyperproliferation-related disorders or disease states an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the nature of the present invention may be more clearly understood preferred forms thereof will now be described by reference to the following non-limiting Examples.

EXAMPLES

Materials and Methods:
Compound Synthesis

Compounds are generally prepared in a 2-step process starting from 2,6-dichloropyrazine.

The first step is a nucleophilic aromatic substitution to generate a monoamino-monohalo intermediate. (Scheme 1).

Scheme 1

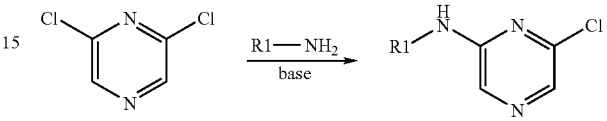

The nucleophilic aromatic substitution is typically carried out by addition of a primary amine to the di-halogenated heterocycle in a solvent such as ethanol, isopropanol, tert-butanol, dioxane, THF, DMF, ethoxyethanol, toluene or xylene. The reaction is typically performed at elevated temperature in the presence of excess amine or a non-nucleophilic base such as triethylamine or diisopropylethylamine, or an inorganic base such as potassium carbonate or sodium carbonate.

Alternatively, the amino substituent may be introduced through a transition metal catalysed amination reaction. Typical catalysts for such transformations include $Pd(OAc)_2/P(t-Bu)_3$, $Pd_2(dba)_3$/BINAP and $Pd(OAc)_2$/BINAP. These reactions are typically carried out in solvents such as toluene or dioxane, in the presence of bases such as caesium carbonate or sodium or potassium tert-butoxide at temperatures ranging from room temperature to reflux.

The amines employed in the first step of the synthesis of these compounds are obtained commercially or are prepared using methods well known to those skilled in the art. Of particular interest are α-alkylbenzylamines which may be prepared through reduction of oximes (Scheme 2). Typical reductants include lithium aluminium hydride, hydrogen gas in the presence of palladium on charcoal catalyst, Zn in the presence of hydrochloric acid, sodium borohydride in the presence of a Lewis acid such as $TiCl_3$, $ZrCl_4$, $NiCl_2$ and $MoO_3$, or sodium borohydride in conjunction with Amberlyst H15 ion exchange resin and LiCl.

Scheme 2

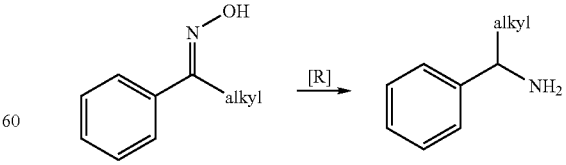

α-Alkylbenzylamines may also be prepared by reductive amination of the corresponding ketones. A classical method for such a transformation is the Leuckart-Wallach reaction, though catalytic conditions or alternative procedures (e.g. NH₄OAc, Na(CN)BH₃) can also be used.

α-Alkylbenzylamines may also be prepared from the corresponding α-alkylbenzyl alcohols. Such methods include derivatisation of the hydroxyl as a mesylate or tosylate and displacement with a nitrogen nucleophile, such as phthalimide or azide which is converted to the primary amine using conventional synthetic methods; or, displacement of the hydroxyl with a suitable nitrogen nucleophile under Mitsunobu-like conditions. α-Alkylbenzyl alcohols can be prepared by reduction of the corresponding ketones with a reducing agent such as sodium borohydride in a solvent such as methanol. Alternatively, α-alkylbenzyl alcohols can be obtained through addition of an alkyl metal species (such as a Grignard reagent) to a benzaldehyde derivative, typically performed at room temperature or below in solvents such as tetrahydrofuran.

α-Alkyl benzylamines of high optical purity may be prepared from chiral α-alkyl benzyl alcohols using the methods outlined above. The chiral α-alkyl benzyl alcohols may be obtained through chiral reduction of the corresponding ketones. Chiral reducing methods are now well known in organic chemistry and include enzymatic processes, asymmetric hydrogenation procedures and chiral oxazaborolidines.

The second step of the synthesis typically involves a palladium mediated cross-coupling of the monoamino-monochloro intermediate with a suitably functionalised coupling partner. Typical coupling partners are boronic acids (Suzuki coupling: see for example Miyaura, N. and Suzuki, Chem Rev. 1995, 952457) or stannanes (Stille coupling: see for example Stille, J. K., Angew. Chem., Int. Ed. Engl., 1986, 25, 508) (Scheme 3).

Scheme 3

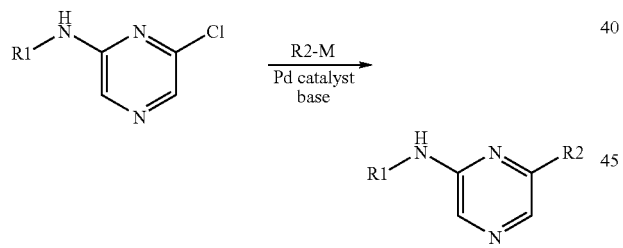

The Suzuki coupling is the preferred coupling method and is typically performed in a solvent such as DME, THF, DMF, ethanol, propanol, toluene, or 1,4-dioxane in the presence of a base such as potassium carbonate, lithium hydroxide, caesium carbonate, sodium hydroxide, potassium fluoride or potassium phosphate. The reaction may be carried out at elevated temperatures and the palladium catalyst employed may be selected from Pd(PPh₃)₄, Pd(OAc)₂, [PdCl₂(dppf)], Pd₂(dba)₃/P(t-Bu)₃, Pd/C.

The products formed from this reaction sequence may be further derivatised using techniques well-known to those skilled in the art. Alternatively, derivatisation of the monoamino mono-chloropyrazine may be undertaken prior to displacement of the 6-chloro substituent. This derivatisation typically involves functionality originally present on the amine species and employs methods well known to those skilled in the art.

Representative syntheses are reported below.

Example 1

1-[4-(Trifluoromethyl)phenyl]butan-1-ol

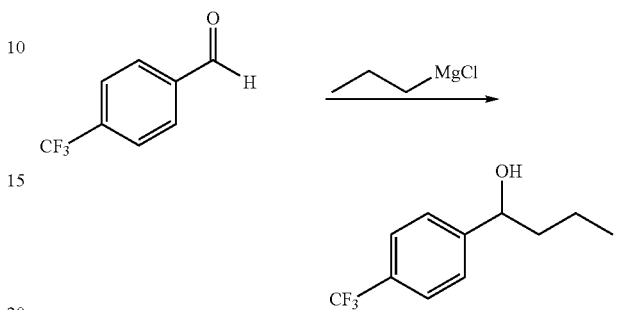

A 2M solution of propylmagnesium chloride in ether (4 ml, 8 mmol) was added to a solution of the aldehyde (1.14 g, 6.6 mmol) in dry THF (10 ml) cooled to 0° C. under N₂. The mixture was stirred for 16 h at room temperature, after which time saturated ammonium chloride solution was added. The product was extracted into ethyl acetate, and the ethyl acetate layer dried and concentrated to furnish pure product (1.4 g, 98%).

¹H-n.m.r. (CDCl₃) δ 0.94 (t, J=7.2 Hz, 3H CH₃), 1.41 (m, 2H, CH₂), 1.75 (m, CH₂, 2H), 4.77 (br s, 1H, CH), 7.44-7.62 (m, 4H, ArH)

Using identical procedures the following compounds were prepared.

| Compound | ¹H-n.m.r. (CDCl₃) |
|---|---|
| CF₃-phenyl-CH(OH)-propyl (meta-CF₃) | δ 0.95(t, J=7.2 Hz, 3H CH₃), 1.39(m, 2H, CH₂), 1.75(m, CH₂, 2H), 4.77(br s, 1H, CH), 7.41-7.63(m, 4H, ArH) |
| 3-methylphenyl-CH(OH)-propyl | δ 0.94(t, J=7.2 Hz, 3H CH₃), 1.40(m, 2H, CH₂), 1.76(m, CH₂, 2H), 2.36(s, 3H, CH₃—Ar), 4.65(m, 1H, CH), 7.07-7.28(m, 4H, ArH) |
| 3,5-dimethoxyphenyl-CH(OH)-propyl | δ 0.93(t, 3H, J=7.2 Hz, CH₃), 1.37(m, 2H, CH₂), 1.75(m, CH₂, 2H), 3.79(s, 6H, 2xCH₃O), 4.61(m, 1H, CH), 6.37(m, 1H, ArH), 6.50(m, 2H, ArH) |
| 2-fluoro-6-chlorophenyl-CH(OH)-propyl | δ 0.96(t, J=7.4 Hz, 3H CH₃), 1.47(m, 2H, CH₂), 1.89(m, CH₂, 2H), 2.36(d, J=4.8 Hz, 1H, 0H), 5.22(m, 1H, CH), 6.93-7.03(m, 1H, Ar—H), 7.16-7.26(m, 2H, Ar—H) |

-continued

| Compound | $^1$H-n.m.r. (CDCl$_3$) |
|---|---|
| [4-(diethylamino)phenyl structure with OH-CH-CH$_2$CH$_2$CH$_3$] | δ 0.93(t, 3H, CH$_3$), 1.16(t, 6H, 2xCH$_3$), 1.2-1.8(m, 4H, 2xCH$_2$), 3.34(q, 4H, 2xCH$_2$), 4.56(m, 1H, CH), 6.65(m, 2H, Ar—H), 7.19(m, 2H, Ar—H). |
| [4-hydroxy-3-methoxyphenyl structure with OH-CH-CH$_2$CH$_2$CH$_3$] | δ 0.93(t, 3H CH$_3$), 1.2-1.8(m, 4H, 2xCH$_2$), 3.48(d, 1H, OH), 3.90(s, 3H, CH$_2$), 4.60 (m, 1H, CH), 5.58(m, 1H, ArOH), 6.80-6.89(m, 3H, Ar—H). |
| [3-cyanophenyl structure with OH-CH-CH$_2$CH$_2$CH$_3$] | δ 0.93(t, J=7.0 Hz, 3H, CH$_3$), 1.24-1.48(m, 2H, CH$_2$), 1.60-1.80(m, 2H, CH$_2$), 1.92 (d, J=3.4 Hz, OH), 4.70-4.78 (m, 1H, CH), 7.41-7.67(m, 4H, ArH) |

Example 2

1-(1-Azidobutyl)-4-(trifluoromethyl)benzene

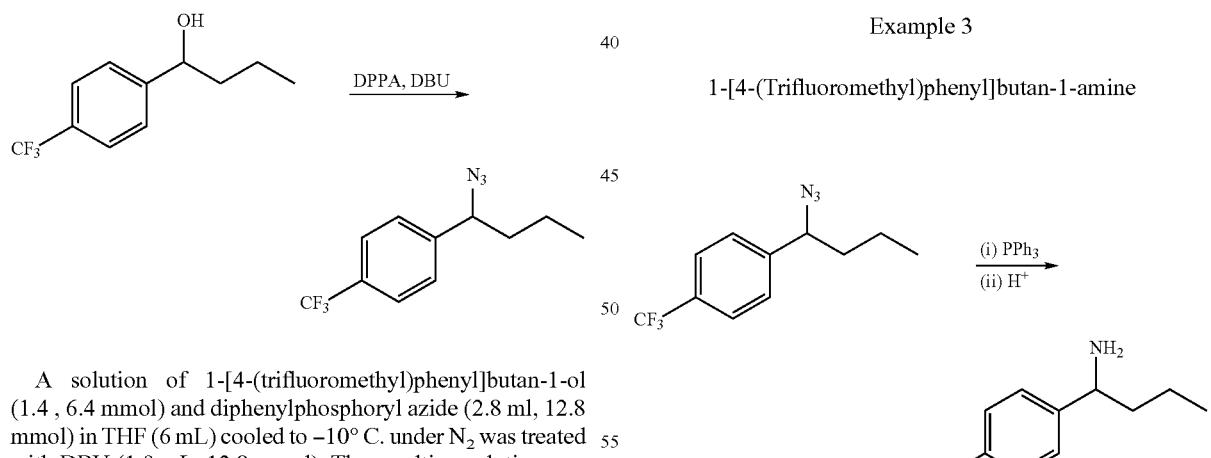

A solution of 1-[4-(trifluoromethyl)phenyl]butan-1-ol (1.4, 6.4 mmol) and diphenylphosphoryl azide (2.8 ml, 12.8 mmol) in THF (6 mL) cooled to −10° C. under N$_2$ was treated with DBU (1.9 mL, 12.8 mmol). The resulting solution was stirred at room temperature for 20 hours and then diluted with a mixture of ether and H$_2$O. The organic phase was dried and concentrated and the residue purified by column chromatography using hexane:diethyl ethyl acetate (10:1) as eluent to furnish pure azide (0.85 g, 54%).

$^1$H-n.m.r. (CDCl$_3$) δ 0.94 (t, J=7.2 Hz, 3H CH$_3$), 1.37 (m, 2H, CH$_2$), 1.75 (m, 2H, CH$_2$), 4.50 (t, 1H, CH), 7.42 (d, J=7.8 Hz, 2H, ArH), 7.64 (d, J=7.8 Hz, 2H, ArH)

Using identical procedures the following compounds were prepared.

| Compound | $^1$H-n.m.r. (CDCl$_3$) |
|---|---|
| [3-(trifluoromethyl)phenyl azidobutyl] | δ 0.94(t, J=7.4 Hz, 3H CH$_3$), 1.38(m, 2H, CH$_2$), 1.76(m, 2H, CH2), 4.50(t, J=7.4 Hz, 1H, CH), 7.48-7.61(m, 4H, ArH) |
| [3-methylphenyl azidobutyl] | δ 0.93(t, J=7.2 Hz, 3H, CH$_3$), 1.36(m, 2H, CH$_2$), 1.76(m, 2H, CH$_2$), 2.37(s, 3H, CH$_3$), 4.37(t, J=7.4 Hz, 1H, CH), 7.07-7.26(m, 4H, Ar—H) |
| [3,5-dimethoxyphenyl azidobutyl] | δ 0.93(t, J=7.4 Hz, 3H, CH$_3$), 1.36(m, 2H, CH$_2$), 1.72(m, 2H, CH$_2$), 3.80(s, 6H, 2xCH$_3$—O), 4.34(t, J=7 Hz, 1H, CH), 6.41-6.45 (m, 3H, Ar—H) |
| [2-fluoro-6-chlorophenyl azidobutyl] | δ 0.96(t, J=7.4 Hz, 3H, CH$_3$), 1.36(m, 2H, CH$_2$), 1.95(m, 2H, CH$_2$), 5.10(t, 1H, OH), 6.98-7.08(m, 1H, Ar—H), 7.18-7.25(m, 2H, Ar—H) |
| [3-cyanophenyl azidobutyl] | δ 0.94(t, J=7.2 Hz, 3H, CH$_3$), 1.22-1.50(m, 2H, CH$_2$), 1.62-1.94(m, 2H, CH$_2$), 4.47(t, J=7.2 Hz, 1H, OH), 7.48-7.64(m, 4H, Ar—H) |

Example 3

1-[4-(Trifluoromethyl)phenyl]butan-1-amine

A mixture of 1-(1-azidobutyl)-(trifluoromethyl)benzene (0.84 g, 3.5 mmol) and triphenylphosphine (1.8 g, 6.9 mmol) in ethyl acetate (6 mL) and 10% HCl (6 ml) was stirred at room temperature for 64 h. The aqueous phase was collected and the organic phase extracted with 10% HCl (3×5 mL). The aqueous layers were combined and basified with 5M NaOH, and then extracted with ethyl acetate (5×15 mL). The organic phase was dried and concentrated to give pure amine (0.4 g, 54%).

¹H-n.m.r. (CDCl₃) δ 0.91 (t, J=7.4 Hz, 3H CH₃), 1.31 (m, 2H, CH₂), 1.62 (m, 2H, CH₂), 3.97 (m, 1H, CH), 7.43 (dd, 2H, Ar—H), 7.58 (dd, 2H, Ar—H)

Using similar procedures the following compounds were prepared.

| Compound | ¹H-n.m.r. (CDCl₃) |
|---|---|
| 3-CF₃-C₆H₄-CH(NH₂)-CH₂CH₂CH₃ | δ 0.91(t, J=7.4 Hz, 3H CH₃), 1.29(m, 2H, CH₂), 1.63(m, 2H, CH₂), 3.98(m, 1H, CH), 7.42-7.59(m, 4H, Ar—H) |
| 3-Me-C₆H₄-CH(NH₂)-CH₂CH₂CH₃ | δ 0.91(t, J=6.8 Hz, 3H CH₃), 1.31(m, 2H, CH₂), 1.62(m, 2H, CH₂), 2.35(s, 3H, CH₃—Ar), 3.84(m, 1H, CH), 7.03-7.21(m, 4H, Ar—H) |
| 3,5-(MeO)₂-C₆H₃-CH(NH₂)-CH₂CH₂CH₃ | δ 0.90(t, J=7.4 Hz, 3H CH₃), 1.30(m, 2H, CH₂), 1.60(m, 2H, CH₂), 3.79(s, 6H, CH₃-Ox2), 3.8(m, 1H, CH), 6.43(m, 1H, Ar—H), 6.47-6.48(m, 2H, Ar—H) |
| 2-F-6-Cl-C₆H₃-CH(NH₂)-CH₂CH₂CH₃ | δ 0.92(t, J=7.4 Hz, 3H CH₃), 1.26(m, 2H, CH₂), 1.85(m, 2H, CH₂), 4.44(t, J=7.4 Hz, 1H, CH), 6.90-7.17(m, 3H, Ar—H) |
| 3-CN-C₆H₄-CH(NH₂)-CH₂CH₂CH₃ | δ 0.91(t, J=7.0 Hz, 3H CH₃), 1.19-1.39(m, 2H, CH₂), 1.47(br s, 2H, NH₂), 1.57-1.68(m, 2H, CH₂), 3.95(t, J=7.0 Hz, 1H, CH), 7.3-7.64(m, 4H, Ar—H) |

Example 4

3-Fluoro-N-methoxy-N-methylbenzamide

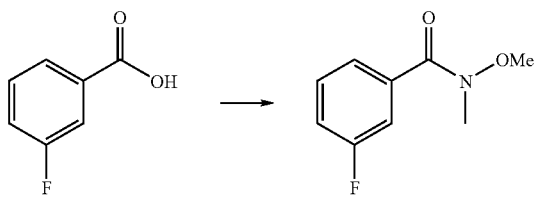

To a suspension of 3-fluorobenzoic acid (140 mg, 1 mmol) and N,O-dimethylhydroxylamine hydrochloride (107 mg, 1.1 mmol) in dichloromethane (2.5 mL) was added 1-[3-(dimethylamino)propyl]-3-ethylcarbodiimide hydrochloride (EDC) (211 mg, 1.1 mmol) and the mixture stirred at room temperature for 75 h. The solvents were removed under reduced pressure and the residue chromatographed using ethyl acetate-hexane (4:6) to separate the pure product (130 mg, 71%).

¹H-n.m.r. (CDCl₃) δ 3.36 (s, 3H, N-Me), 3.55 (s, 3H, N—OMe), 7.1.-7.2 (m, 1H, Ar), 7.3-7.5 (m, 3H, Ar)

Using similar procedures the following compounds were prepared.

| Compound | ¹H-n.m.r. (CDCl₃) |
|---|---|
| nicotinoyl-N(Me)(OMe) | δ 3.38(s, 3H, N—Me), 3.55(s, 3H, N—OMe), 7.3-7.4(m, 1H, pyr), 7.95-8.05(m, 1H, pyr), 8.65-8.70 (m, 1H, pyr), 8.94(d, J=1.6 Hz, 1H, pyr) |
| 4-F-C₆H₄-C(O)-N(Me)(OMe) | δ 3.36(s, 3H, N—Me), 3.55(s, 3H, N—OMe), 7.03-7.12(m, 2H, Ar), 7.70-7.7(m, 2H, Ar) |
| 4-HO-C₆H₄-C(O)-N(Me)(OMe) | δ 3.35(s, 3H, N—Me), 3.57(s, 3H, N—OMe), 6.85(d, J=8.8 Hz, 2H, Ar), 7.63(d, J=8.8 Hz, 2H, Ar) |
| 3-HO-C₆H₄-C(O)-N(Me)(OMe) | δ 3.34(s, 3H, N—Me), 3.57(s, 3H, N—OMe), 6.93-6.97(m, 1H, Ar), 7.12-7.26(m, 3H, Ar) |

Example 5

1-(3Fluorophenyl)butan-1-one

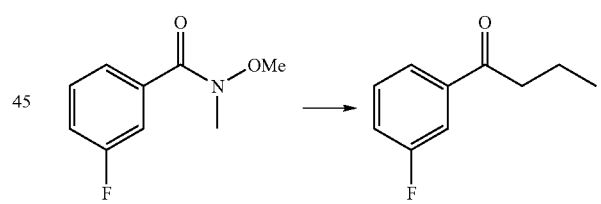

To a solution of 3-fluoro-N-methoxy-N-methylbenzamide (130 mg, 0.71 mmol) in dry THF (2 mL) cooled to −10° C. was added propyl magnesium chloride (532 μl, 2M solution in ether, 1.1 mmol) under nitrogen. The solution was stirred at −10° C. for 1 h and at room temperature for 75 min. The solution was the poured into saturated aqueous ammonium chloride and the product extracted into ethyl acetate (3×25 mL). The organic layers were combined, washed with brine, dried (MgSO₄) and concentrated to give a pale yellow oil, which was purified by chromatography using ethyl acetate-hexane (1:9) to separate the pure product (78 mg, 66%).

¹H-n.m.r. (CDCl₃) δ 1.01 (t, J=7.4 Hz, 3H, Me), 1.77 (sep, 2H, CH₂CH₃), 2.93 (t, J=7.2 Hz, 2H, COCH₂), 7.15-7.30 (m, 1H, Ar), 7.35-7.50 (m, 1H, Ar), 7.60-7.70 (m, 1H, Ar), 7.70-7.80 (m, 1H, Ar.

Using similar procedures the following compounds were prepared.

| Compound | $^1$H-n.m.r. (CDCl$_3$) |
|---|---|
| 1-(pyridin-3-yl)butan-1-one | δ 1.02(t, J=7.4 Hz, 3H, Me), 1.80 (sep, 2H, CH$_2$CH$_3$), 2.97(t, J=7.2 Hz, 2H, COCH$_2$), 7.36-7.46 (m, 1H, pyr), 8.20-8.30(m, 1H, pyr), 8.7(br d J=4 Hz, 1H, pyr), 9.18(br s, 1H, pyr). |
| 1-(4-fluorophenyl)butan-1-one | δ 1.00(t, J=7.4 Hz, 3H, Me), 1.76 (sep, 2H, CH$_2$CH$_3$), 2.91(t, J=7.2 Hz, 2H, COCH$_2$), 7.11(t, J=8.5 Hz, 2H, Ar), 7.94-8.02(m, 2H, Ar) |
| 1-(3-chlorophenyl)butan-1-one | δ 1.01(t, J=7.4 Hz, 3H, Me), 1.68-1.86(m, 2H, CH$_2$CH$_3$), 2.92 (t, J=7.4 Hz, 2H, COCH$_2$), 7.36-7.55(m, 2H, Ar), 7.82-7.93 (m, 3H, Ar) |
| 1-(4-bromophenyl)butan-1-one | δ 1.00(t, J=7.4 Hz, 3H, Me), 1.67-1.85(m, 2H, CH$_2$CH$_3$), 2.91 (t, J=7.4 Hz, 2H, COCH$_2$), 7.59(d, J=8.8 Hz, 2H, Ar), 7.82(d, J=8.8 Hz, 2H, Ar) |
| 1-(4-hydroxyphenyl)butan-1-one | δ 1.00(t, J=7.4 Hz, 3H, Me), 1.68-1.86(m, 2H, CH$_2$CH$_3$), 2.91 (t, J=7.4 Hz, 2H, COCH$_2$), 6.55(br s, 1H, OH), 6.92(d, J=9.2 Hz, 2H, Ar), 7.92(d, J=9.2 Hz, 2H, Ar) |

Example 6

1-(3-Chlorophenyl)butan-1-amine

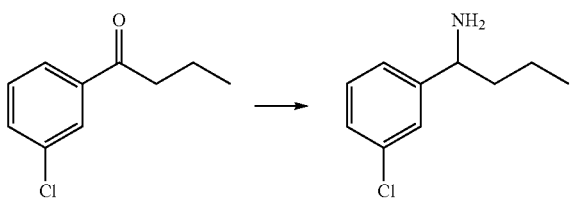

To a solution of 1-(3-fluorophenyl)butan-1-one (430 mg, 2.4 mmol) and ammonium acetate (1.09 g, 14.1 mmol) in methanol (10 mL) under nitrogen was added sodium cyanoborohydride (2.35 ml, 1M solution in THF, 2.35 mmol). The solution was stirred at room temperature for 38 h. after which time conc. HCl was added to give a pH~2. After bubbling had ceased the solvent was removed under reduced pressure and the residue dissolved in ethyl acetate and water. The organic phase was collected and the aqueous phase washed with ethyl acetate (20 mL). The aqueous phase was basified to pH~10 with solid KOH and the product extracted into ethyl acetate (3×20 mL). The organic layers were combined, washed with brine, dried (Na$_2$SO$_4$) and concentrated to give a pure product (120 mg, 28%).

$^1$H-n.m.r. (CDCl$_3$) δ 0.90 (t, J=7.2 Hz, 3H, CH$_2$CH$_2$CH$_3$), 1.17-1.44 (m, 2H CH$_2$CH$_2$CH$_3$), 1.58-1.69 (m, 2H, CH$_2$CH$_2$CH$_3$), 1.81 (brs, 2H, NH$_2$), 3.88 (t, J=6.8 Hz, CHNH$_2$), 7.20-7.32 (m, 4H, Ar)

Using similar procedures the following compounds were prepared.

| Compound | $^1$H-n.m.r. (CDCl$_3$) |
|---|---|
| 1-(4-hydroxyphenyl)butan-1-amine | δ 0.89(t, J=7.2 Hz, 3H, CH$_2$CH$_2$CH$_3$), 1.16-1.38(m, 2H, CH$_2$CH$_2$CH$_3$), 1.57-1.69 (m, 2H, CH$_2$CH$_2$CH$_3$), 7.74-2.14(brs, 2H, NH$_2$), 3.85(brs, 1H, CHNH$_2$), 6.78(d, J=8.6 Hz, 2H, Ar), 7.17 (d, J=8.6 Hz, 2H, Ar) |
| 1-(3-hydroxyphenyl)butan-1-amine | δ 0.88(t, J=7.4 Hz, 3H, CH$_2$CH$_2$CH$_3$), 1.18-1.39(m, 2H, CH$_2$CH$_2$CH$_3$), 1.57-1.69 (m, 2H, CH$_2$CH$_2$CH$_3$), 3.79(t, J=6.8 Hz, 1H, CHNH$_2$), 6.74-6.84 (m, 1H, Ar), 7.10-7.19 (m, 1H, Ar) |
| 3-methyl-1-phenylbutan-1-amine | δ 0.88-0.94(m, 6H, 2xMe), 1.47-1.56(m, 5H, CH$_2$CH(CH$_3$) NH$_2$), 3.95(t, J=6.6 Hz, 1H, CH$_2$NH$_2$), 7.20-7.37 (m, 5H, Ar) |
| 1-(4-(2-(diethylamino)ethoxy)phenyl)ethan-1-amine | δ 1.07(t, J=7.1 Hz, 6H, 2xCH$_2$CH$_3$), 1.36(d, J=6.2 Hz, 3H, CHMe), 2.64(q, 4H, 2xCH$_2$CH$_3$), 2.87(t, J=6.3 Hz, 2H, OCH$_2$CH$_2$N), 4.01-4.07(m, 3H, OCH$_2$CH$_2$N + CHMe), 6.86(d, J=8.7 Hz, 2H, Ar), 7.25(d, J=8.7 Hz, 2H, Ar). |
| 1-(3-fluorophenyl)butan-1-amine | δ 0.91(t, J=7.4 Hz, 3H, Me), 1.18-1.41(m, 2H, CH$_2$CH$_3$), 1.57-1.68(m, 4H, COCH$_2$ + NH), 3.90 (t, J=6.8 Hz, 1H, CHNH$_2$), 6.90-7.15(m, 3H, Ar), 7.22-7.33(m, 1H, Ar). |
| 1-(4-fluorophenyl)butan-1-amine | δ 0.89(t, 3H, Me), 1.14-1.40(m, 2H, CH$_2$CH$_3$), 1.55-1.70(m, 4H, COCH$_2$), 3.88(t, J=6.8 Hz, 1H, CHNH$_2$), 6.90-7.10(m, 2H, Ar), 7.23-7.30(m, 2H, Ar). |
| 1-(4-chlorophenyl)butan-1-amine | δ 0.89(t, J=7.4 Hz, 3H, CH$_2$CH$_2$CH$_3$), 1.18-1.38(m, 2H, CH$_2$CH$_2$CH$_3$), 1.48-1.67 (m, 4H, CH$_2$CH$_2$CH$_3$, NH$_2$), 3.87(t, J=6.8 Hz, 1H, CHNH$_2$), 7.21-7.31 (m, 4H, Ar) |

| Compound | $^1$H-n.m.r. (CDCl$_3$) |
|---|---|
| 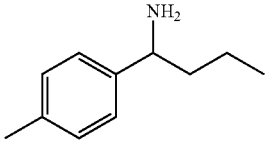 | δ 0.90(t, J=7.2 Hz, 3H, CH$_2$CH$_2$CH$_3$), 1.21-1.40(m, 2H, CH$_2$CH$_2$CH$_3$), 1.48(brs, 2H, NH$_2$), 1.57-1.69(m, 2H, CH$_2$CH$_2$CH$_3$), 2.33 (s, 3H, Ar—Me), 3.85(t, J=7.0 Hz, 1H, CHNH$_2$), 7.11-7.26(m, 4H, Ar) |
| 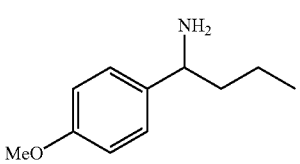 | δ 0.90(t, J=7.4 Hz, 3H, CH$_2$CH$_2$CH$_3$), 1.17-1.35(m, 2H, CH$_2$CH$_2$CH$_3$), 1.43(brs, 2H, NH$_2$), 1.56-1.68(m, 2H, CH$_2$CH$_2$CH$_3$), 3.80 (s, 3H, OMe), 3.84(t, J=6.8 Hz, 1H, CHNH$_2$), 6.86(d, J=8.6 Hz, 2H, Ar) 7.24(d, J=8.6 Hz, 2H, Ar) |

Example 7

3-Amino-3-phenylpropan-1-ol

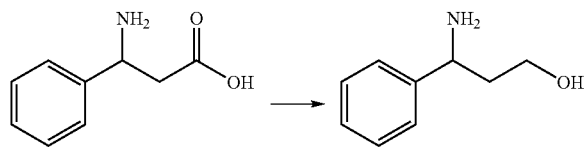

To a suspension of 3-amino-3-phenylpropanoic acid (2.0 g, 12.1 mmol) in dry THF (45 mL) cooled to 0° C. under N$_2$ was added portionwise over 20 minutes solid LiAlH$_4$ (920 mg, 24.2 mmol). Stirring was continued at room temperature for 24 h. after which time solid Na$_2$SO$_4$.10H$_2$O was added with stirring until only a heavy white precipitate was present. The organic layer was diluted with ether and filtered through Celite® and the concentrated in vacuo. The residue was dissolved in ethyl acetate (50 mL) and extracted with 1N HCl (3×40 mL). The aqueous layers were combined and basified to pH~12 with 5M NaOH. The aqueous phase was extracted with ethyl acetate (3×50 mL) and the combined organic phases dried (Na$_2$SO$_4$) and concentrated in vacuo to separate the product which was used without further purification (0.9 g, 49%).

$^1$H-n.m.r. (CDCl$_3$) δ 1.84-1.94 (m, 2H, CH$_2$CH$_2$OH), 2.68 (br s, 1H, NH$_2$), 3.79 (t, J=5.8 Hz, 2H, CH$_2$CH$_2$OH), 4.08.4.15 (m, 1H, CHNH$_2$), 4.77 (q, 1H, CH), 7.21-7.38 (m, 5H, Ar—H)

Example 8

6-Chloro-N-[1-(4-methylphenyl)butyl]pyrazin-2-amine

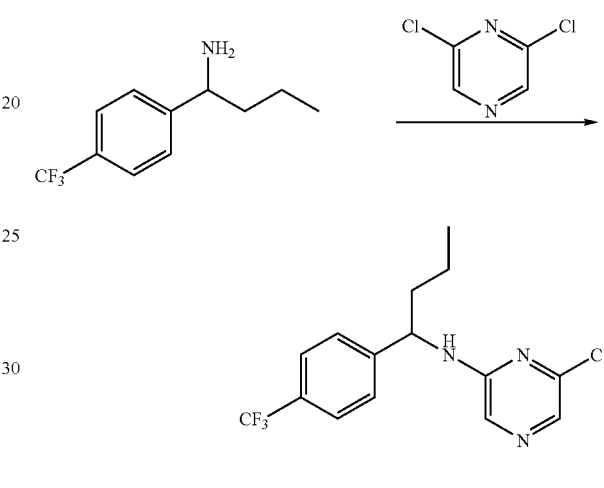

To a solution of 1-[4-(trifluorormethyl)phenyl]butan-1-amine (0.40 g, 1.9 mmol) and 2,6-dichloropyrazine (0.55 g, 3.7 mmol) in 1,4-dioxane (6 mL) was added anhydrous potassium carbonate (0.39 g, 2.8 mmol). The resulting mixture was heated at reflux for 18 h. After cooling to room temperature, the mixture was diluted with ethyl acetate and H$_2$O. The organic phase was collected, dried and concentrated. The residue was purified by flash chromatography eluting with ethyl acetate-hexane (1:1) to give pure product (0.03 g, 5%).

$^1$H-n.m.r. (CDCl$_3$) δ 0.95 (t, J=7.4 Hz, 3H CH$_3$), 1.39 (m, 2H, CH$_2$), 1.81 (m, 2H, CH$_2$), 4.77 (q, 1H, CH), 5.09 (br d, 1H, NH), 7.42-7.62 (m, 5H, Ar—H), 7.80 (s, 1H, pyraz.-H)

Using similar procedures the following compounds were prepared.

| Compound | $^1$H-n.m.r. (CDCl$_3$) |
|---|---|
| 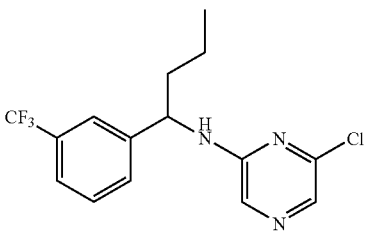 | δ 0.95(t, J=7.4 Hz, 3H, CH$_3$), 1.39(m, 2H, CH$_2$), 1.82(m, 2H, CH$_2$), 4.78(q, 1H, CH), 5.12(br d, 1H, NH), 7.41-7.81(m, 6H, Ar—H). |

-continued

| Compound | ¹H-n.m.r. (CDCl₃) |
|---|---|
| (4-MeS-phenyl)-CH(propyl)-NH-(6-chloropyrazin-2-yl) | δ 0.94(t, J=7.4 Hz, 3H CH₃), 1.37(m, 2H, CH₂), 1.81(m, 2H, CH₂), 2.46(s, 3H, CH₃—S), 4.51(q, 1H, CH), 4.63(q, 1H, CH), 5.09(d, 1H, NH), 7.23(s, 4H, Ar—H), 7.58(s, 1H, pyraz-H), 7.77(s, 1H, pyraz-H). |
| (2-Cl-6-F-phenyl)-CH(propyl)-NH-(6-chloropyrazin-2-yl) | δ 0.95(t, J=7.4 Hz, 3H, CH₃), 1.37(m, 2H, CH₂), 1.95(m, 2H, CH₂), 5.45(m, 2H, CH +NH), 6.90-7.18(m, 3H, Ar—H), 7.76(s, 2H, Ar—H) |
| (3,5-diMeO-phenyl)-CH(propyl)-NH-(6-chloropyrazin-2-yl) | δ 0.93(t, J=7.4 Hz, 3H CH₃), 1.38(m, 2H, CH₂), 1.78(m, 2H, CH₂), 3.76(s, 6H, CH₃—O), 4.57(q, J=6 Hz, 1H, CH), 5.15(d, 1H, NH), 6.35(m, 1H, Ar—H), 6.46(m, 2H, Ar—H), 7.60(s, 1H, pyraz-H), 7.77(s, 1H, pyraz-H). |
| (phenyl)-CH(isobutyl)-NH-(6-chloropyrazin-2-yl) | δ 0.96(t, J=6.6 Hz, 6H, 2xMe), 1.58-1.80(m, 3H, CH₂CH₂Me), 4.67-4.77(m, 1H, CHNH), 5.10(br d, J=6.8 Hz, 1H, NH), 7.21-7.33(m, 5H, Ar) 7.60(s, 1H, pyraz-H), 7.77(s, 1H, pyraz-H) |
| (diphenyl)CH-NH-(6-chloropyrazin-2-yl) | δ 5.38(br s, 1H, CHNH), 5.95(br d, J=6.2 Hz, 1H, NH), 7.21-7.39(m, 10H, 2xPh) 7.68(s, 1H, pyraz-H), 7.83(s, 1H, pyraz-H |
| (4-HO-phenyl)-CH(propyl)-NH-(6-chloropyrazin-2-yl) | δ 0.93(t, J=7.4 Hz, 3H, CH₂CH₂CH₃), 1.17-1.44(m, 2H, CH₂CH₂CH₃), 1.63-1.73(m, 2H, CH₂CH₂CH₃), 4.51-4.62(m, 1H, CHNH), 5.10(br d, J=6.4 Hz, 1H, NH), 6.76(d, J=8.8 Hz, 2H, Ar), 7.00(d, J=8.8 Hz, 1H, Ar), 7.16(d, J=8.8 Hz, 2H, Ar), 7.58(s, 1H, pyraz-H), 7.77(s, 1H, pyraz-H) |

-continued

| Compound | ¹H-n.m.r. (CDCl₃) |
|---|---|
| 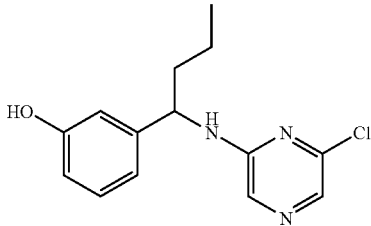 | δ 0.93(t, J=7.4 Hz, 3H, CH₂CH₂CH₃), 1.26-1.44(m, 2H, CH₂CH₂CH₃), 1.73-1.85(m, 2H, CH₂CH₂CH₃), 4.52-4.63(m, 1H, CHNH), 5.22(br d, J=6.8 Hz, 1H, NH), 6.69-6.87(m, 3H, Ar), 7.14-7.22(m, 1H, Ar), 7.57(s, 1H, pyraz-H), 7.76(s, 1H, pyraz-H) |
| 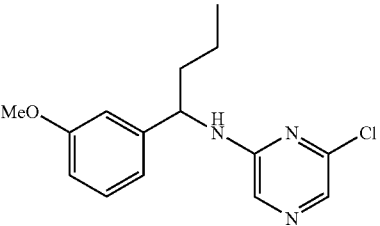 | δ 0.94(t, J=7.4 Hz, 3H, Me), 1.30-1.49(m, 2H, CH₂), 1.75-1.88 (m, 2H, CH₂), 3.79(s, 3H, OMe), 4.62(q, J=7.2 Hz, 1H, CHCH₂CH₂CH₃), 5.13(br d, J=6.8 Hz, 1H, NH₂), 6.78-6.92 (m, 3H, Ar), 7.21-7.29(m, 1H, Ar), 7.60(s, 3H, pyraz-H), 7.77(s, 1H, pyraz-H) |
| 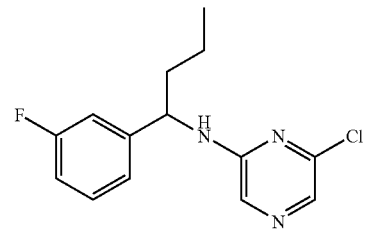 | δ 0.94(t, J=7.4 Hz, 3H, Me), 1.27-1.46(m, 2H, CH₂), 1.75-1.86 (m, 2H, CH₂), 4.69(q, J=7.0 Hz, 1H, CHCH₂CH₂CH₃), 5.16 (br d, J=6.8 Hz, 1H, NH), 6.90-7.12(m, 3H, Ar), 7.24-7.35(m, 1H, Ar), 7.61(s, 1H, pyraz-H), 7.79(s, 1H, pyraz-H) |
| 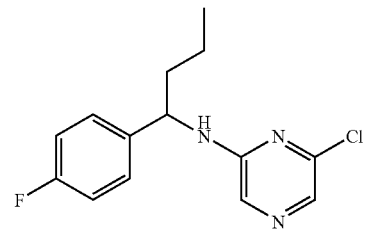 | δ 0.93(t, J=7.4 Hz, 3H, Me), 1.25-1.47(m, 2H, CH₂), 1.70-1.87 (m, 2H, CH₂), 4.66(q, J=7.1 Hz, 1H, CHCH₂CH₂CH₃), 5.13 (br d, J=6.6 Hz, 1H, NH), 6.97-7.05(m, 2H, Ar), 7.59-7.78(m, 2H, Ar), 7.59(s, 1H, pyraz-H), 7.78(s, 1H, pyraz-H) |
| 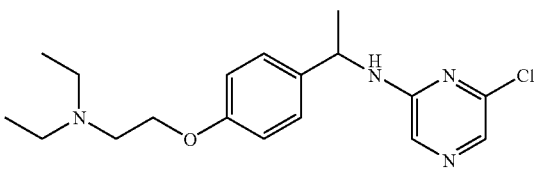 | δ 1.07(t, J=7.4 Hz, 6H, 2xCH₂CH₃), 1.55(d, J=6.8 Hz, 3H, CHCH₃), 2.64(q, 4H, 2xCH₂CH₃), 2.87(t, J=6.4 Hz, 2H, OCH₂CH₂N), 4.03(t, J=6.4 Hz, 2H, OCH₂CH₂N), 4.80-4.85 (m, 1H, CHMe), 5.03(br d, J=6.8 Hz, 1H, NH), 6.87(d, J=8.6 Hz, 2H, Ar), 7.25(d, J=8.6 Hz, 2H, Ar), 7.60(s, 3H, pyraz-H), 7.78(s, 1H, pyraz-H) |
| 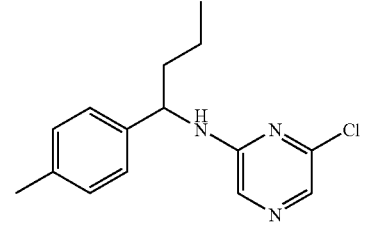 | δ 0.93(t, J=7.4 Hz, 3H, CH₂CH₂CH₃), 1.26-1.44(m, 2H, CH₂CH₂CH₃), 1.74-1.88(m, 2H, CH₂CH₂CH₃), 2.32(s, 3H, Ar—Me), 4.57—4.67(m, 1H, CHNH), 5.10(br d, J=6.2 Hz, NH), 7.11-7.20(m, 4H, Ar), 7.58(s, 1H, pyraz-H), 7.76(s, 1H, pyraz-H) |
| 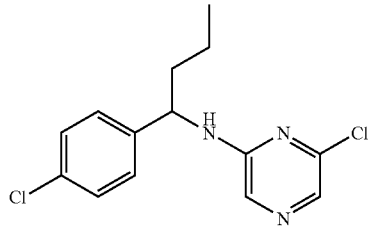 | δ 0.94(t, J=7.4 Hz, 3H, CH₂CH₂CH₃), 1.26-1.45(m, 2H, CH₂CH₂CH₃), 1.74-1.87(m, 2H, CH₂CH₂CH₃), 4.61-4.71(m, 1H, CHNH), 5.06(br d, J=6.4 Hz, NH), 7.23-7.33(m, 4H, Ar), 7.58(s, 1H, pyraz-H), 7.79(s, 1H, pyraz-H) |

| Compound | ¹H-n.m.r. (CDCl₃) |
|---|---|
| (4-methoxyphenyl-butyl-NH-chloropyrazine structure) | δ 0.93(t, J=7.4 Hz, 3H, CH₂CH₂CH₃), 1.26-1.43(m, 2H, CH₂CH₂CH₃), 1.74-1.88(m, 2H, CH₂CH₂CH₃), 3.78(s, 3H, OMe), 4.55(m, 1H, CHNH), 5.08(br d, J=6.8 Hz, 1H, NH), 6.86(d, J=8.6 Hz, 2H, Ar), 7.23(d, J=8.6 Hz, 2H, Ar), 7.58(s, 1H, pyraz-H), 7.76(s, 1H, pyraz-H) |
| (3-hydroxy-1-phenylpropyl-NH-chloropyrazine structure) | δ 2.04-2.15(m, 2H, CH₂CH₂OH), 3.74(t, J=4.8 Hz, 2H, CH₂CH₂OH), 4.98-5.08(m, 1H, CHNH), 5.69(br d, J=7.0 Hz, 1H, NH), 7.39(m, 5H, Ar), 7.66(s, 1H, pyraz-H), 7.77(s, 1H, pyraz-H) |
| (3-aminophenyl-butyl-NH-chloropyrazine structure) | δ 0.94(t, J=7.2 Hz, 3H, Me), 1.27-1.46(m, 2H, CH₂), 1.74-1.86 (m, 2H, CH₂), 3.66(br s, 2H, NH₂), 4.48-4.59(m, 1H, CHCH₂CH₂CH₃), 5.06(br d, J=7.0 Hz, 1H, NH), 6.54-6.71 (m, 3H, Ar), 7.11(t, J=7.8 Hz, 1H, Ar), 7.60(s, 1H, pyraz-H), 7.77(s, 1H, pyraz-H) |
| (3-cyanophenyl-butyl-NH-chloropyrazine structure) | δ 0.96(t, J=7.3 Hz, 3H, Me), 1.26-1.51(m, 2H, CH₂), 1.77-1.90 (m, 2H, CH₂), 4.77(q, J=6.8 Hz, 1H, CHCH₂CH₂CH₃), 5.07 (d, J=7.4 Hz, 1H, NH), 7.41-7.63(m, 4H, Ar), 7.64(s, 1H, pyraz-H), 7.81(s, 1H, pyraz-H) |

Example 9

N-(3-{1-[(6-Chloropyrazin-2-yl)amino]butyl}phenyl)acetamide

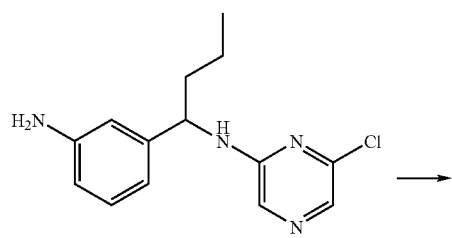

→

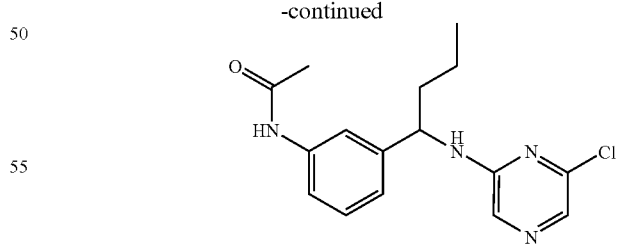

To a stirred solution of N-[1-(3-aminophenyl)butyl]-6-chloropyrazin-2-amine (0.10 g, 0.36 mmol) and triethylamine (100 μl, 0.72 mmol) in dichloromethane (3 mL) cooled to 0° C. was added acetyl chloride (31 μL, 0.43 mmol). The resulting mixture was stirred at room temperature for 18 h. then diluted with dichloromethane (10 mL) and washed with H₂O (10 mL) and brine (10 mL). The organic phase was collected, dried and concentrated and the residue purified by flash chromatography eluting with ethyl acetate-hexane (1:1) to give pure product (94 mg, 82%).

¹H-n.m.r. (CDCl₃) δ 0.93 (t, J=7.4 Hz, 3H, Me), 1.28-1.43 (m, 2H, CH₂), 1.76-1.85 (m, 2H, CH₂), 2.16 (s, 3H, COCH₃), 4.48-4.59 (m, 1H, CHCH₂CH₂CH₃), 5.15 (br d, J=6.8 Hz, 1H, NH), 7.06 (d, J=7.4 Hz, 1H, Ar), 7.23-7.33 (m, 3H, Ar), 7.54 (s, 1H, CONH), 7.60 (s, 1H, pyraz-H), 7.77 (s, 1H, pyraz-H).

Example 10

6-Chloro-N-[1-(4-methylphenyl)butyl]pyrazin-2-amine

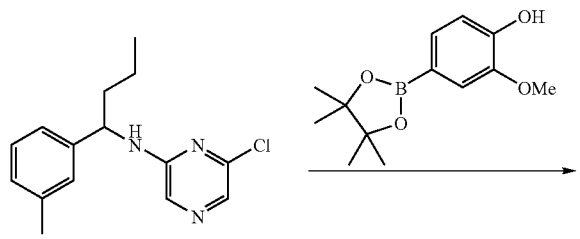

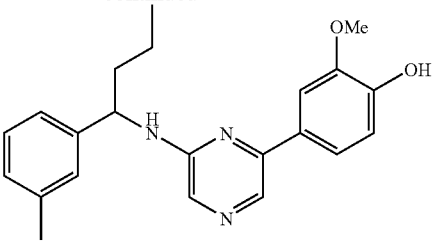

Under a nitrogen atmosphere a mixture of 6-chloro-N-[1-(3-methylphenyl)butyl]pyrazin-2-amine (0.21 g, 0.76 mmol), 4-(4,4,5,5-tetramethyl-1,3,2-dioxaborolan-2-yl)phenol (0.23 g, 91 mmol), tetrakis(triphenylphosphine)palladium(0) (90 mg, 0.08 mmol) in toluene-n-propanol (4 mL, 3:1) was treated with 2M aqueous sodium carbonate solution (0.4 mL, 0.84 mmol). The resulting mixture was stirred vigorously whilst being heated under reflux for 22 hours. Once cool ethyl acetate was added and the mixture dried (MgSO₄) and filtered. Removal of solvent in vacuo then yielded crude product, which was purified by column chromatography using dichloromethane:diethyl ether (90:10) as eluent to furnish (0.165 g, 60%).

¹H-n.m.r. (CDCl₃) δ 0.95 (t, 3H, CH₃), 1.42 (m, 2H, CH₂), 1.82 (m, 2H, CH₂), 2.33 (s, 3H, CH₃—Ar), 3.94 (s, 3H, CH₃-0), 4.75 (m, 1H, CH), 5.09 (d, 1H, NH), 6.25 (br s, 1H, OH), 6.94-7.50 (m, 7H, Ar—H), 7.66 (s, 1H, pyraz.-H), 8.20 (s, 1H, pyraz.-H).

Using similar procedures the following compounds were prepared.

| Compound | ¹H-n.m.r. (CDCl₃) | m/z (ES) |
|---|---|---|
| *4-MeS-phenyl analog* | δ 0.95(t, 3H, CH₃), 1.42(m, 2H, CH₂), 1.85(m, 2H, CH₂), 2.45(s, 3H, CH₃—S), 3.94(s, 3H, CH₃-0), 4.75(q, 1H, CH), 5.01 (d, 1H, NH), 5.96(br s, 1H, 0H), 6.94-7.44 (m, 7H, Ar—H), 7.65(s, 1H, py-H), 8.20 (s, 1H, py-H). | |
| *3,5-diMeO-phenyl analog* | δ 0.95(t, 3H, CH₃), 1.43(m, 2H, CH₂), 1.84(m, 2H, CH₂), 3.76(s, 6H, 2xCH3O), 3.94(s, 3H, CH₃O), 4.70(q, 1H, CH), 5.03 (d, 1H, NH), 6.07(br s, 1H, OH). | |
| *4-CF₃-phenyl analog* | δ 0.98(t, 3H, CH₃), 1.43(m, 2H, CH₂), 1.87(m, 2H, CH₂), 3.92(s, 3H, CH₃O), 4.94(m, 2H, CH + NH), 6.96(d, 1H, Ar—H), 7.36-7.64(m, 6H, Ar—H), 7.69(s, 1H, pyraz.-H), 8.22(s, 1H, pyraz.-H). | |

| Compound | ¹H-n.m.r. (CDCl₃) | m/z (ES) |
|---|---|---|
| [structure: 2-chloro-6-fluorophenyl butyl-NH-pyrazine-methoxyphenol] | δ 0.95(t, 3H, CH₃), 1.42(m, 2H, CH₂), 1.82(m, 2H, CH₂), 2.33(s, 3H, CH₃—Ar), 3.94(s, 3H, CH₃-O), 4.74(q, 1H, CH), 5.29 (d, 1H, NH), 6.25(br s, 1H, OH), 6.94-7.50 (m, 7H, Ar—H), 7.66(s, 1H, pyraz.-H), 8.20(s, 1H, pyraz.-H). | |
| [structure: 3,5-dimethoxyphenyl butyl-NH-pyrazine-methoxyphenol] | δ 0.93(t, J=7.4 Hz, 3H CH₃), 1.38(m, 2H, CH₂), 1.78(m, 2H, CH₂), 3.76(s, 6H, CH₃—O), 4.57(q, J=6 Hz, 1H, CH), 5.15(d, 1H, NH), 6.35(m, 1H, Ar—H), 6.46(m, 2H, Ar—H), 7.60(s, 1H, pyraz-H), 7.77(s, 1H, pyraz-H). | |
| [structure: 3-fluorophenyl butyl-NH-pyrazine-methoxyphenol] | δ 0.96(t, J=7.4 Hz, 3H, CH₂CH₂CH₃), 1.35-1.51(m, 2H, CH₂CH₂CH₃), 1.78-1.92(m, 2H, CH₂CH₂CH₃), 3.94(s, 3H, OMe), 4.76-4.86(m, 1H, CHNH), 5.01(br d, J=6.0 Hz, 1H, NH), 5.91(br s, 1H, OH), 6.96(d, J=8.0 Hz, 1H, Ar), 7.06-7.42(m, 6H, Ar) 7.72 (br s, 1H, pyraz-H), 8.22(br s, 1H, pyraz-H) | 368 (M + H)⁺ |
| [structure: 4-fluorophenyl butyl-NH-pyrazine-methoxyphenol] | δ 0.96(t, J=7.1 Hz, 3H, CH₂CH₂CH₃), 1.30-1.48(m, 2H, CH₂CH₂CH₃), 1.73-1.93(m, 2H, CH₂CH₂CH₃), 3.94(s, 3H, OMe), 4.73-4.83(m, 1H, CHNH), 5.02(br d, J=6.4 Hz, 1H, NH), 6.02(br s, 1H, OH), 6.94-7.05 (m, 3H, Ar), 7.30-7.44(m, 4H, Ar), 7.66(s, 1H, pyraz-H), 8.21(s, 1H, pyraz-H) | 368 (M + H)⁺ |
| [structure: 4-chlorophenyl butyl-NH-pyrazine-methoxyphenol] | δ 0.95(t, J=7.4 Hz, 3H, CH₂CH₂CH₃), 1.30-1.48(m, 2H, CH₂CH₂CH₃), 1.72-1.95(m, 2H, CH₂CH₂CH₃), 3.91(s, 3H, OMe), 4.72-4.82(m, 1H, CHNH), 5.07(br d, J=6.2 Hz, 1H, NH), 6.25(br s, 1H, OH), 6.95(d, J=8.6 Hz, 1H, Ar), 7.29(br s, 4H, Ar), 7.39-7.42(m, 2H, Ar), 7.76(s, 1H, pyraz-H), 8.21(s, 1H, pyraz-H) | 384 (M + H)⁺ |
| [structure: 4-methylphenyl butyl-NH-pyrazine-methoxyphenol] | δ 0.95(t, J=7.4 Hz, 3H, CH₂CH₂CH₃), 1.30-1.52(m, 2H, CH₂CH₂CH₃), 1.75-1.94(m, 2H, CH₂CH₂CH₃), 2.32(s, 3H, Ar—Me), 3.95 (s, 3H, OMe), 4.70-4.80(m, 1H, CHNH), 5.03(br d, J=6.6 Hz, 1H, NH), 6.04 (br s, 1H, OH), 6.96(d, J=8.2 Hz, 1H, Ar), 7.13(d, J=8.1 Hz, 1H, Ar), 7.26(d, J=8.1 Hz, 1H, Ar), 7.65(s, 1H, pyraz-H), 8.19 (s, 1H, pyraz-H) | 364 (M + H)⁺ |

-continued

| Compound | ¹H-n.m.r. (CDCl₃) | m/z (ES) |
|---|---|---|
| (structure) | δ 0.95(t, J=7.4 Hz, 3H, CH₂CH₂CH₃), 1.29-1.51(m, 2H, CH₂CH₂CH₃), 1.73-1.93(m, 2H, CH₂CH₂CH₃), 3.77(s, 3H, OMe), 3.95(s, 3H, OMe), 4.68-4.78(m, 1H, CHNH), 5.03(br d, J=6.2 Hz, 1H, NH), 6.10(br s, 1H, OH), 6.85(d, J=8.4 Hz, 2H, Ar), 6.96(d, J=8.4 Hz, 1H, Ar), 7.28(d, J=8.4 Hz, 2H, Ar), 7.40-7.49(m, 2H, Ar), 7.65(s, 1H, pyraz-H), 8.20(s, 1H, pyraz-H) | 380 (M + H)⁺ |
| (structure) | δ 0.96(t, J=7.2 Hz, 3H, CH₂CH₂CH₃), 1.39-1.50(m, 2H, CH₂CH₂CH₃), 1.79(m, 2H, CH₂CH₂CH₃), 3.78(s, 3H, OMe), 3.94(s, 3H, OMe), 4.71-4.81(m, 1H, CHNH), 5.02(br d, J=6.0 Hz, NH), 5.98(s, 1H, OH), 6.74-6.80(m, 1H, Ar), 6.96(d, J=8.4 Hz, 1H, Ar), 7.20-7.28(m, 1H, Ar), 7.41-7.48(m, 2H, Ar), 7.67(s, 1H, pyraz-H), 8.20(s, 1H, pyraz-H) | 380 (M + H)⁺ |
| (structure) | δ 1.07(t, J=7.2 Hz, 6H, 2xCH₂CH₃), 1.58(d, J=6.4 Hz, 3H, CHCH₃), 2.64(q, J=7.2 Hz, 4H, 2xCH₂CH₃), 2.87(t, J=6.4 Hz, 2H, OCH₂CH₂N), 3.94(s, 3H, OMe), 4.03(t, J=6.4 Hz, 2H, OCH₂CH₂N), 4.88-4.97(m, 2H, CHMe + NH), 6.84-6.98(m, 3H, Ar), 7.26-7.49(m, 4H, Ar), 7.65(s, 1H, pyraz-H), 8.21(s, 1H, pyraz-H) | 437 (M + H)⁺ |
| (structure) | δ 0.96(d, J=9.5 Hz, 3H, CH₂(CH₃)CH₃), 0.99(d, J=9.9 Hz, 3H, CH(CH₃)CH₃), 1.63-1.86(m, 3H, CH(CH₃)CH₃ and CH₂), 3.94(s, 3H, OMe), 4.83-4.94(m, 1H, CHNH), 5.01(brd, J=7.0 Hz, 1H, NH), 6.05(brs, 1H, OH), 6.96(d, J=8.4 Hz, 1H, Ar), 7.22-7.48(m, 7H, Ar), 7.67(s, 1H, pyraz-H), 8.19(s, 1H, pyraz-H) | 364 (M + H)⁺ |
| (structure) | δ 0.94(t, J=7.2 Hz, 3H, CH₂CH₂CH₃), 1.32-1.47(m, 2H, CH₂CH₂CH₃), 1.76-1.90(m, 2H, CH₂CH₂CH₃), 3.94(s, 3H, OMe), 4.57-4.68(m, 1H, CHNH), 5.11(br d, J=6.2 Hz, 1H, NH), 6.70(d, J=8.5 Hz, 2H, Ar), 6.96(d, J=7.6 Hz, 1H, Ar), 7.16(d, J=8.5 Hz, 2H, Ar), 7.41-7.49(m, 2H, Ar), 7.62(s, 1H, pyraz-H), 8.19(s, 1H, pyraz-H) | 366 (M + H)⁺ |
| (structure) | δ 0.94(t, J=7.4 Hz, 3H, CH₂CH₂CH₃), 1.33-1.49(m, 2H, CH₂CH₂CH₃), 1.76-1.90(m, 2H, CH₂CH₂CH₃), 3.94(s, 3H, OMe), 4.65-4.75(m, 1H, CHNH), 5.04(br d, J=6.2 Hz, 1H, NH), 6.68-6.73(m, 1H, Ar), 6.82-6.98(m, 3H, Ar), 7.17(t, J=7.8 Hz, 1H, Ar), 7.45-7.47(m, 2H, Ar), 7.62(s, 1H, pyraz-H), 8.18(s, 1H, pyraz-H) | 366 (M + H)⁺ |

| Compound | ¹H-n.m.r. (CDCl₃) | m/z (ES) |
|---|---|---|
| 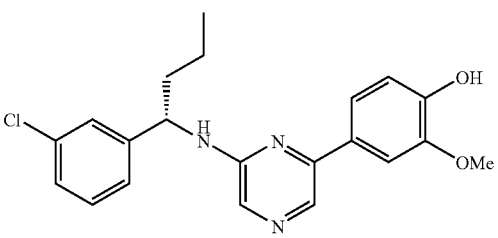 | δ 0.96(t, J 7.2 Hz, 3H, CH₂CH₂CH₃), 1.39-1.50(m, 2H, CH₂CH₂CH₃), 1.77-1.92(m, 2H, CH₂CH₂CH₃), 3.94(s, 3H, OMe), 4.74-4.84(m, 1H, CHNH), 4.99(br d, J 6.0 Hz, 1H, NH), 5.87(br s, 1H, OH), 6.96(d, J 8.8 Hz, 1H, Ar), 7.69(br s, 1H, pyr), 8.24 (br s, 1H, pyr) | 384 (M + H)⁺ |
| 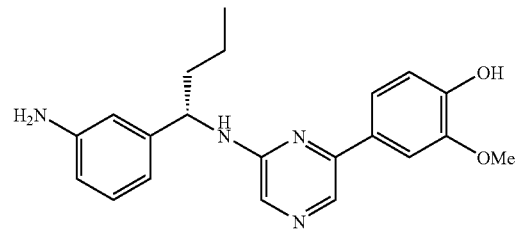 | δ 0.95(t, J=7.4 Hz, 3H, CH₂CH₂CH₃), 1.35-1.50(m, 2H, CH₂CH₂CH₃), 1.77-1.88(m, 2H, CH₂CH₂CH₃), 3.64(br s, 2H, NH₂), 3.96(s, 3H, OMe), 4.67(q, J=6.8 Hz, 1H, CH), 4.99(br d, J=6.8 Hz, 1H, NH), 5.95 (br s, 1H, OH), 6.53-6.58(m, 1H, Ar), 6.68 (m, 1H, Ar), 6.75-6.78(m, 1H, Ar), 6.97(d, J=8.4 Hz, 1H, Ar), 7.10(t, J=7.8 Hz, 1H, Ar), 7.41-7.55(m, 2H, Ar), 7.66(s, 1H, pyraz-H), 8.20(s, 1H, pyraz-H) | 365 (M + H)⁺ |
| 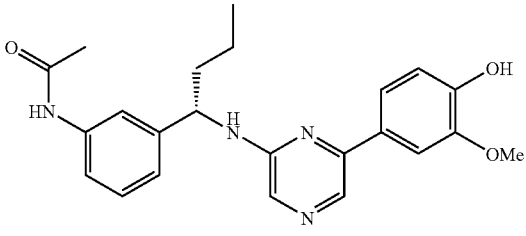 | δ 0.96(t, J=7.2 Hz, 3H, Me), 1.35-1.52(m, 2H, CH₂), 1.80-1.92(m, 2H, CH₂), 2.14(s, 3H, COCH₃), 3.95(s, 3H, OMe), 4.78(q, J=6.8 Hz, 1H, CH), 5.02(br d, J=6.2 Hz, 1H, NH), 5.80(s, 1H, OH), 6.96(d, J=7.8 Hz, 1H, Ar), 7.11-7.22(m, 2H, Ar), 7.30-7.47 (m, 4H, Ar), 7.57(s, 1H, CONH), 7.67(s, 1H, pyraz-H), 8.20(s, 1H, pyraz-H). | |
| 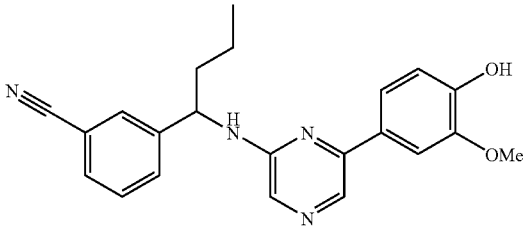 | δ 0.97(t, J=7.4 Hz, 3H, Me), 1.33-1.52(m, 2H, CH₂), 1.76-1.89(m, 2H, CH₂), 3.94(s, 3H, OCH₃), 4.88(q, J=6.8 Hz, 1H, CHCH₂CH₂CH₃), 5.07(d, J=7.4 Hz, 1H, NH), 6.96(d, J=7.8 Hz, 1H, Ar), 7.35-7.46 (m, 3H, Ar), 7.51-7.56(m, 1H, Ar), 7.60-7.65 (m, 1H, Ar), 7.68-7.71(m, 2H, Ar + pyraz-H), 8.23(s, 1H, pyraz-H) | |
| 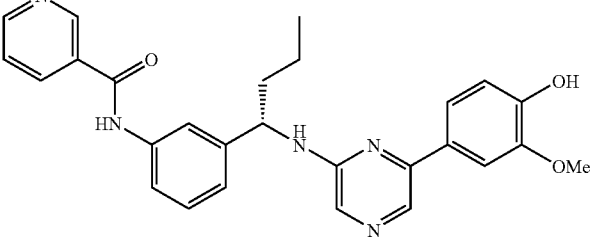 | δ 0.93(t, J=7.4 Hz, 3H, Me), 1.32-1.52(m, 2H, CH₂), 1.78-1.92(m, 2H, CH₂), 3.88(s, 3H, OMe), 4.79(q, J=6.8 Hz, 1H, CH), 5.25 (br d, J=6.2 Hz, 1H, NH), 6.45(br s, 1H, OH), 6.91(d, J=8.4 Hz, 1H, Ar), 7.15-7.53 (m, 6H, Ar), 7.63(s, 1H, pyraz-H), 7.71(br s, 1H, CONH), 8.10-8.17(m, 1H, pyr-H), 8.14(s, 1H, pyraz-H), 8.51(m, 1H, pyr-H), 8.67(dd, 1H, J=4.8, 2.0 Hz, 1H, pyr-H), 9.06(d, 1H, J=2.0Hz, 1H, pyr-H). | |
| 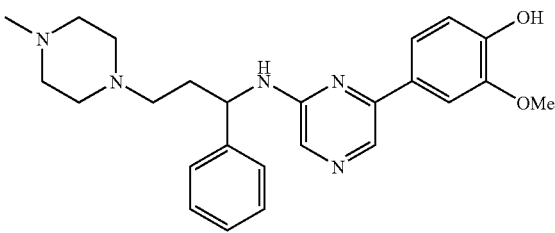 | δ 1.84-2.17(m, 2H, CH₂), 2.34(s, 3H, NMe), 2.50-2.56(m, 10H, CH₂N), 3.85(s, 3H, OMe), 4.96-5.03(m, 1H, CHNH), 6.90 (d, J=7.8 Hz, 1H, Ar), 7.20-7.47(m, 7H, Ar), 7.71(s, 1H, pyraz-H), 8.15(s, 1H, pyraz-H) | |

Example 11

3,5-Dichloro-2-methylpyrazine

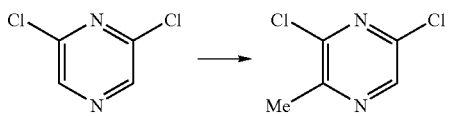

To a solution of n-butyllithium (3.8 mL, 2.5M in hexane, 9.4 mmol) in THF (40 mL) cooled to −30° C. under nitrogen was added 2,2,6,6-tetramethylpiperidine (1.7 mL, 10.1 mmol). This solution was allowed to warm to 0° C. over 20 min. and was then cooled to −70° C. A solution of 2,6-dichloropyrazine (1 g, 6.7 mmol) in THF (40 mL) was added dropwise and the resulting brown solution stirred at −70° C. for 30 min. Iodomethane (4.1 mL, 67 mmol) was then added and the solution stirred at −70° C. for a further 45 min after which time a mixture of ethanol (5 mL), THF (5 mL) and 1N HCl (1 mL) was added. The solution was allowed to warm to room temperature and was concentrated under reduced pressure. The residue was dissolved in $H_2O$ (50 mL) and the product extracted into dichloromethane (3×30 mL). The combined organic layers were washed with $H_2O$ (50 mL) and brine (50 mL) and dried ($Na_2SO_4$). The organic layer was concentrated in vacuo and the residue purified by column chromatography eluting with dichloromethane-hexane (1:1) to separate the product as a clear motile oil (820 mg).

$^1$H-n.m.r. ($CDCl_3$) δ2.65 (s, 3H, $CH_3$), 8.41 (s, 1H, pyraz.-H).

Example 12

4-(6-{[(1S)-1-(3-Fluorophenyl)butyl]amino}pyrazin-2-yl)-2-methoxyphenyl dihydrogen phosphate

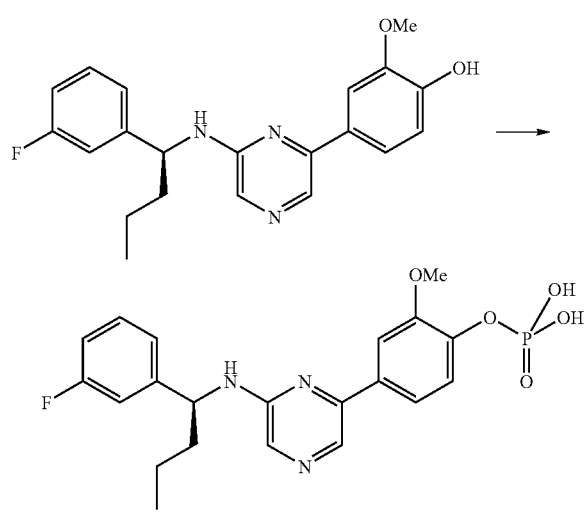

A degassed solution of the phenol (0.25 g; 0.72 mmol) in anhydrous $CH_3CN$ (30 ml) was cooled to −10° C., $CBr_4$ (1.19 g; 3.60 mmol) was added and the mixture stirred for 10 min before adding N,N-diisopropylethylamine (0.20 g; 1.51 mmol) and 4-pyrrolidinylpyridine (0.011 g; 0.072 mmol). A minute later, dropwise addition of dibenzylphosphonate (0.27 g; 1.04 mmol) was commenced. The exothermic reaction was controlled by the rate of addition of the phosphonate and further cooling, keeping the internal temperature at or below −10° C. The reaction mixture became light yellow, and was stirred at −10° C. until it was judged complete by TLC (approx. 45 min). Aqueous $KH_2PO_4$ (0.5M, 32 ml/100 ml $CH_3CN$) was added and the mixture extracted with EtOAc (3×100 ml). The combined organic extracts were washed successively with water (1×50 mL), brine (1×75 mL) and dried ($Na_2CO_3/Na_2SO_4$) and concentrated in vacuo. Chromatography of the residue on neutral alumina, eluting with a petroleum ether/ethyl acetate gradient mixture afforded the dibenzyl phosphonate ester in 74% yield. $^1$H NMR (200 MHz, DMSO-d6) δ0.96 (t, J=7.4 Hz, 3H, $CH_2CH_2CH_3$), 1.52-1.23 (m, 2H, $CH_2CH_2CH_3$), 1.93-1.75 (m, 2H, $CH_2CH_2CH_3$), 3.84 (s, 3H, $OCH_3$), 4.87-4.83 (m, 1H, $NHCHCH_2$), 5.16 (s, 2H, $PhCH_2$), 5.17 (d, J=7.8 Hz, 1H, NH), 5.20 (s, 2H, $CH_2$), 6.97-6.87 (m, 1H, ArH), 7.48-7.06 (m, 16H, ArH), 7.77 (s, 1H, pyraz.-H), 8.20 (s, 1H, pyraz.-H).

To a nitrogen-purged solution of the dibenzyl phosphonate (0.95 g; 1.51 mmol) in methanol (100 ml) was added 10% Pd/C (250 mg) and the mixture was hydrogenated on a Parr Hydrogenator overnight. Upon cooling to RT, the reaction mixture was filtered through Celite®. The solids were washed with MeOH (3×50 ml) and the MeOH and combined filtrates was removed under reduced pressure, leaving behind a yellow solid that was re-crystallized from MeOH/$Et_2O$ to afford the desired product, 0.48 g; 71%.

m/z (ES) 448.22; (M+1).

Screening

Compound Dilution

For screening purposes, compounds were diluted in 96 well plates at a concentration of 20 μM. Plates were warmed at 37° C. for 30 minutes before assay.

Establishment of TEL:JAK Cell Lines

The coding region encompassing nucleotides 1-487 of TEL was amplified by PCR using the oligonucleotides STEL (5'-GGA GGATCC TGA TCT CTC TCG CTG TGA GAC-3') (SEQ ID NO:1) and 3TEL (5'-AGGC GTCGAC TTC TTC TTC ATG GTT CTG-3') (SEQ ID NO:2) and U937 mRNA as template. A BamH I site was present into the STEL Primer, a Sal I site was incorporated into the 3TEL primer. The regions encompassing the kinase domains of JAK2 (nucleotides 2994-3914; JAK2F 5'-ACGC GTC GAC GGT GCC TTT GAA GAC CGG GAT-3'(SEQ ID NO:3) ; JAK2R 5'-ATA GTT TAGCGGCCG CTC AGA ATG AAG GTC ATT T-3') (SEQ ID NO:4) and JAK3 (nucleotides 2520-3469; JAK3F 5'-GAA GTC GAC TAT GCC TGC CAA GAC CCC ACG ATC TT-3'(SEQ ID NO:5); JAK3R 5'-GGA TCTAGA CTA TGA AAA GGA CAG GGA GTG GTG TTT -3') (SEQ ID NO:6) were generated by PCR using Taq DNA Polymerase (Gibco/BRL) and U937 mRNA as template. A SalI site was incorporated into the forward primer of JAK2 and JAK3, a Not I site was incorporated into the JAK2 reverse primer and a Xba I site was added to the reverse primer of JAK3.

A TEL/Jak2 fusion was generated by digestion of the TELPCR product with BamH I/Sal I, digestion of the JAK2 PCR product with Sal I/Not I followed by ligation and subcloning into the mammalian expression Vector pTRE 2 (Clontech) digested with BamH I-Not I (pTELJAK2). For JAK3 Sal I/Not I cleaved kinase domain PCR product was ligated with BamH I/Sal I cleaved TELproduct followed by ligation into BamH I/Not I cleaved pTRE2 (pTELJAK3).

The growth factor dependent myelomonocytic cell line $BaF_3$ bearing the pTET-off plasmid (Clontech) was transfected with either pTELJAK2 or pTELJAK3 and the cells selected for factor independent growth. BaF 3 wild type cells were cultured in DMEM 10% FCS, 10% WEHI 3B conditioned medium. BaP3 TEL/JAK cells were cultured in DMEM 10% Tet-System Approved FBS (without WEHI 3B conditioned medium).

Growth and Maintenance of Cancer Cell Lines

K562 (Chronic Myeloid Leukemia), PC3 (Prostate Cancer), and DU145 (Prostate Cancer) were obtained from the American Type Culture Collection (ATCC). K562 was grown in RPMI, with 10% FBS with Glutamx added. DU145 cells were cultured in DMED, with 10% FBS and Glutamx and MEM non-essential amino acids added. PC3 cells were grown in F12K medium, with 10% FBS and Glutamx and MEM non-essential amino acids added. All cells were grown at 37° C. in 5% $CO_2$.

Cellular Assays were Performed as Follows:

Cell suspensions were prepared by harvesting cells from culture. (Cells used in this test should be in later log phase growth and high viability.) Cells were diluted in correct growth medium to 1.1× final concentration (from 50000 cell/mL to 200,000 cell/mL, depending on cell line).

Compounds to be tested were added (10 μL, 10× final concentration) to a flat bottom 96-well plate. The cellular suspension (90 μL per well) was added, and the plate incubated for 40 hr at 37° C., 5% $CO_2$. MTT (20 μL per well, 5 mg/mL in PBS) was added and the plates were returned to the incubator for a further 6 hours. Lysis buffer (100 μL per well, 10% SDS, 0.01N HCl) was added and the plate stored in the incubator overnight. The plate was then read at 590 nm.

Tubulin Assay

Turbidometric assays of microtubule assembly were performed by incubating microtubule protein in cuvettes at 37° C. in a thermostatically controlled spectrophotometer measuring the change in absorbance at 340 nm over time. The microtubule protein was incubated with the each test compound at 0° C. and polymerisation was initiated by addition of 1 mM GTP, prior to heating to 37° C.

Results

The activity of a range of compounds is shown in Table 1. Compounds that exhibited a capacity to inhibit 50% of cellular growth at a concentration of 20 μM or less are designated as "+". Likewise, compounds which inhibited tubulin polymerisation by greater than 50% at 50 μM are designated as "+"; compounds which did not inhibit tubulin polymerisation by 50% at 50 μM are designated as "−"; and compounds which were not tested are designated as "NT".

TABLE 1

| CHEMISTRY | DU145 | PC3 | K562 | TelJak2 | TelJak3 | Tubulin |
|---|---|---|---|---|---|---|
| 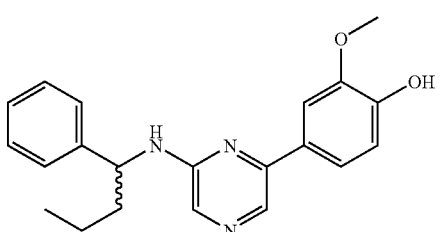 C21H23N3O2 | + | + | + | + | + | + |
| 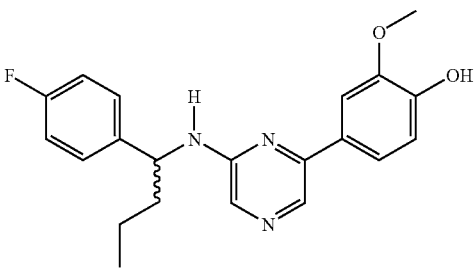 C21H22FN3O2 | + | − | + | + | + | + |
| 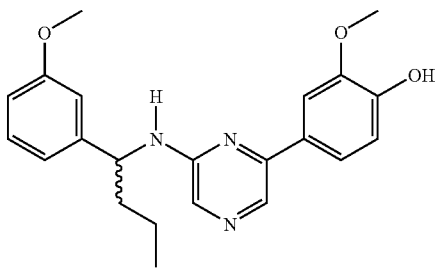 C22H25N3O3 | + | + | + | + | + | + |

TABLE 1-continued
| CHEMISTRY | DU145 | PC3 | K562 | TelJak2 | TelJak3 | Tubulin |
|---|---|---|---|---|---|---|
| 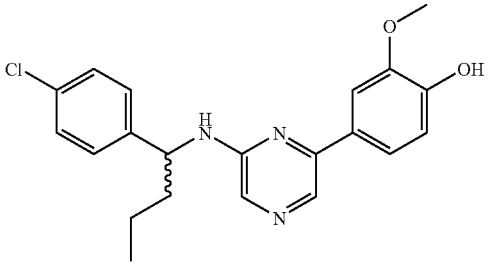<br>C21H22ClN3O2 | + | + | + | + | + | + |
| 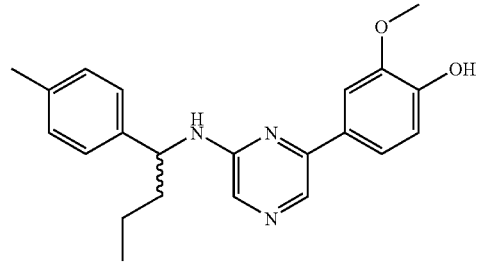<br>C22H25N3O2 | + | + | + | + | + | + |
| 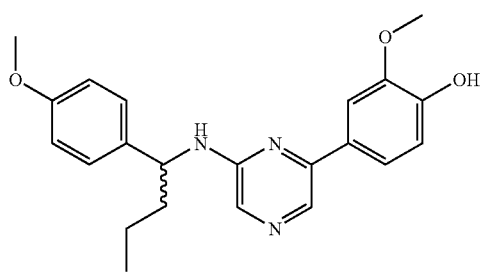<br>C22H25N3O3 | + | + | + | + | + | + |
| 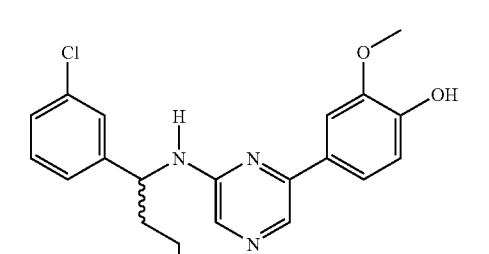<br>C21H22ClN3O2 | + | + | + | + | + | + |
| 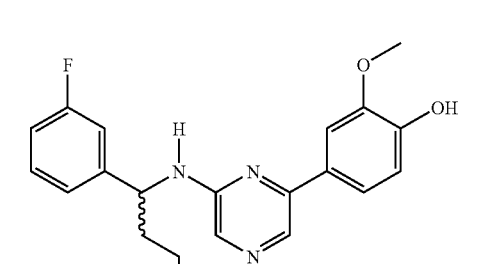<br>C21H22FN3O2 | + | + | + | + | + | + |

TABLE 1-continued
| CHEMISTRY | DU145 | PC3 | K562 | TelJak2 | TelJak3 | Tubulin |
|---|---|---|---|---|---|---|
| 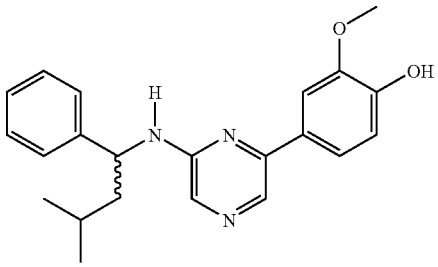<br>C22H25N3O2 | − | − | + | + | + | NT |
| 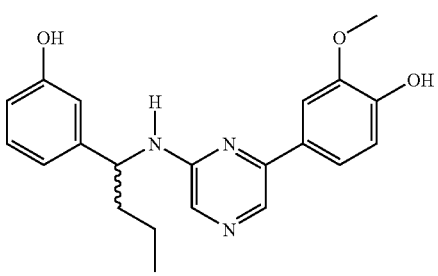<br>C21H23N3O3 | − | − | + | + | + | + |
| 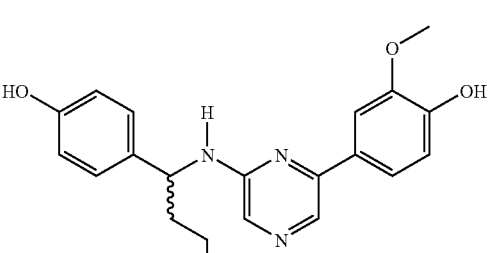<br>C21H23N3O3 | − | − | − | + | + | NT |
| 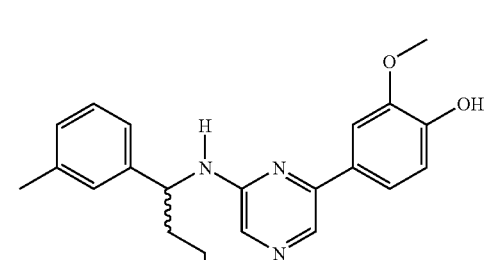<br>C22H25N3O2 | + | + | + | + | + | + |
| 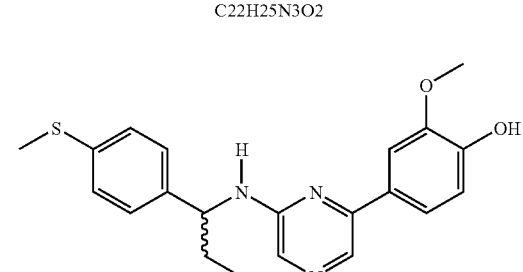<br>C22H25N3O2S | − | − | + | + | + | NT |

TABLE 1-continued
| CHEMISTRY | DU145 | PC3 | K562 | TelJak2 | TelJak3 | Tubulin |
|---|---|---|---|---|---|---|
| 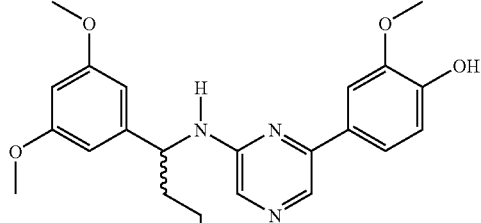<br>C23H27N3O4 | + | + | + | + | + | + |
| 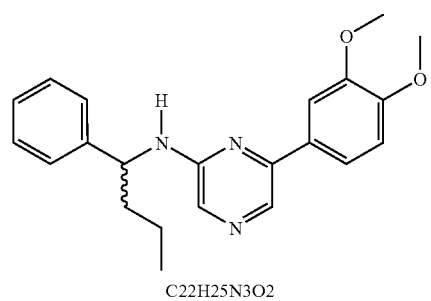<br>C22H25N3O2 | + | + | + | + | + | + |
| 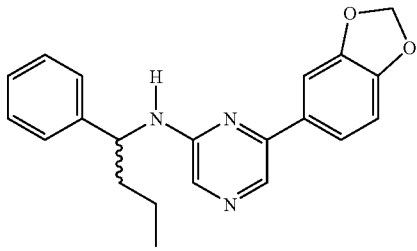<br>C21H21N3O2 | + | + | + | + | + | + |
| 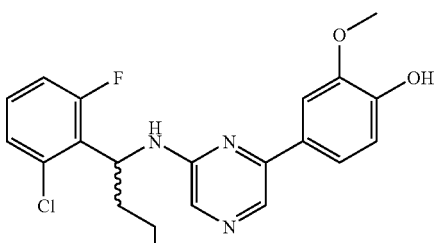<br>C21H21ClFN3O2 | + | + | + | + | + | + |
| 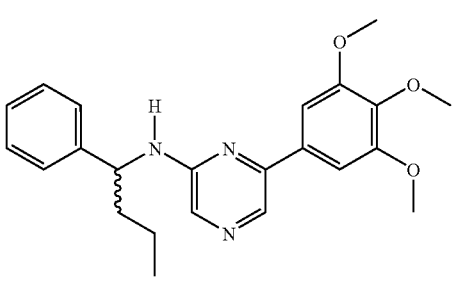<br>C23H27N3O3 | + | − | + | + | + | NT |

TABLE 1-continued
| CHEMISTRY | DU145 | PC3 | K562 | TelJak2 | TelJak3 | Tubulin |
|---|---|---|---|---|---|---|
| 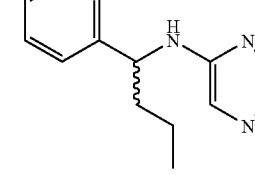 C22H22F3N3O2 | − | − | − | − | − | − |
| 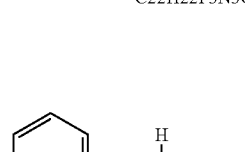 C21H23N3O | − | − | + | + | + | NT |
| 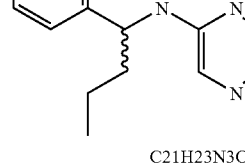 C20H22N4O2 | + | + | + | + | + | + |
| 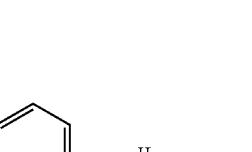 C21H22FN3O2 | + | + | + | + | + | + |
| 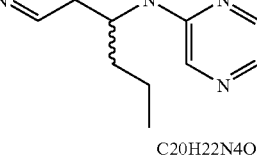 C22H22F3N3O2 | + | + | + | + | + | + |

US 8,084,456 B2
TABLE 1-continued
| CHEMISTRY | DU145 | PC3 | K562 | TelJak2 | TelJak3 | Tubulin |
|---|---|---|---|---|---|---|
| 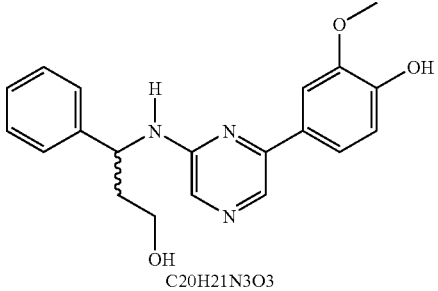<br>C20H21N3O3 | − | − | − | + | + | NT |
| 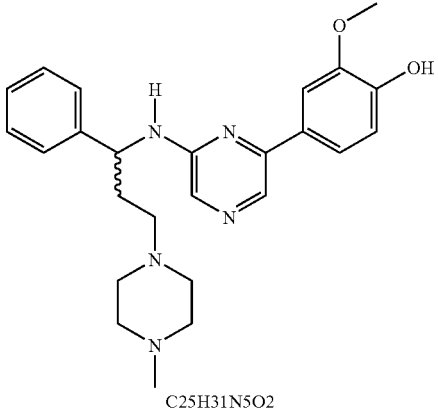<br>C25H31N5O2 | + | + | + | + | + | + |
| 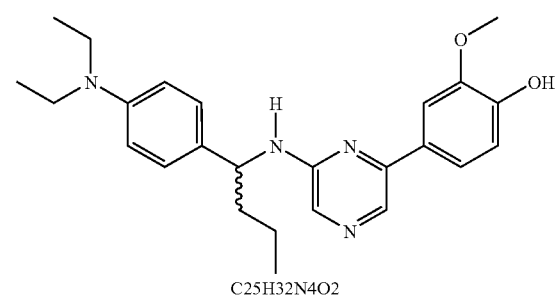<br>C25H32N4O2 | + | − | − | + | + | NT |
| 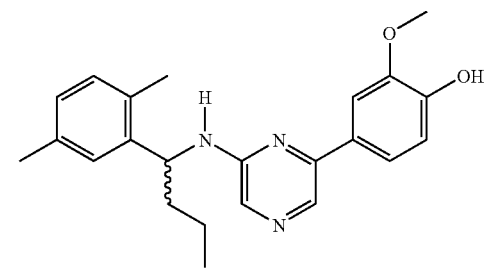<br>C23H27N3O2 | + | + | + | + | + | + |
| 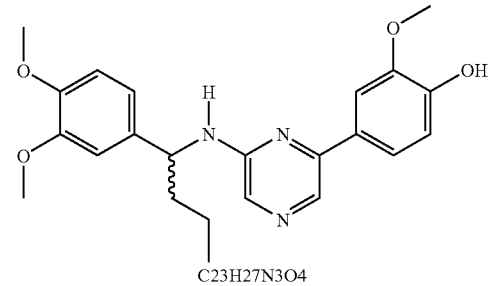<br>C23H27N3O4 | + | − | + | + | + | NT |

TABLE 1-continued
| CHEMISTRY | DU145 | PC3 | K562 | TelJak2 | TelJak3 | Tubulin |
|---|---|---|---|---|---|---|
| 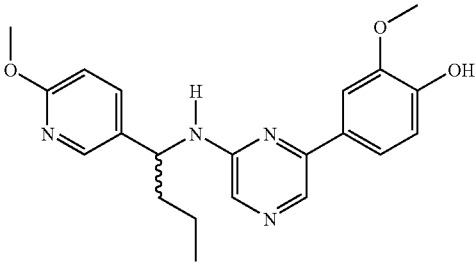 C21H24N4O3 | + | − | + | + | + | + |
| 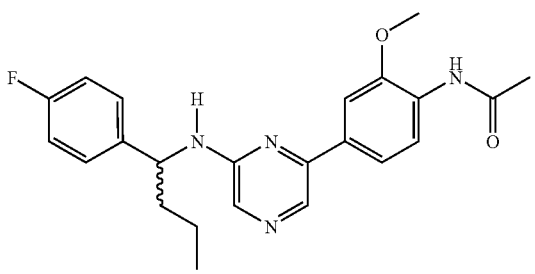 C23H25FN4O2 | + | + | + | + | + | + |
| 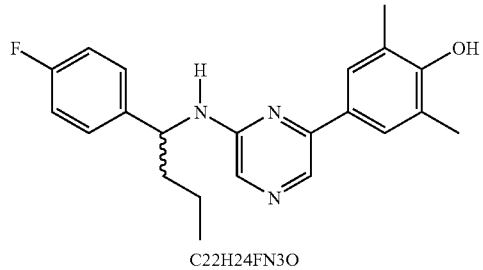 C22H24FN3O | + | + | + | + | + | + |
| 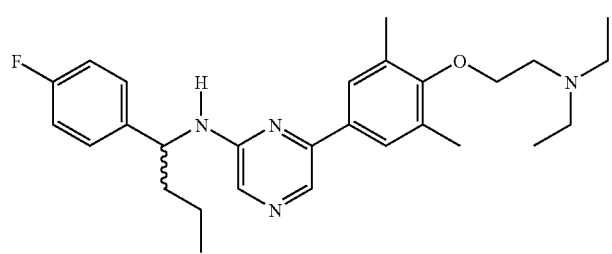 C28H37FN4O | + | + | + | + | + | + |
| 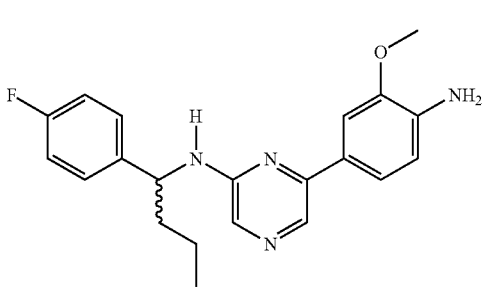 C21H23FN4O | + | + | + | + | + | + |

TABLE 1-continued
| CHEMISTRY | DU145 | PC3 | K562 | TelJak2 | TelJak3 | Tubulin |
|---|---|---|---|---|---|---|
| 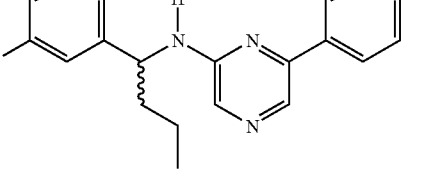<br>C21H24N4O2 | − | + | + | + | + | + |
| 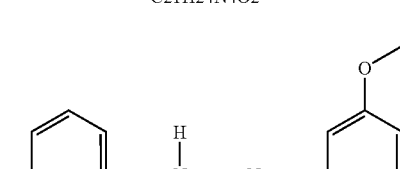<br>C23H26N4O3 | − | − | + | + | + | NT |
| 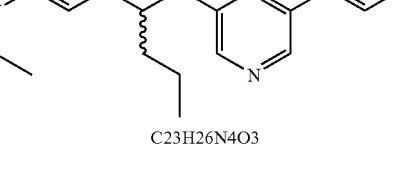<br>C22H22N4O2 | − | + | + | + | + | NT |
| 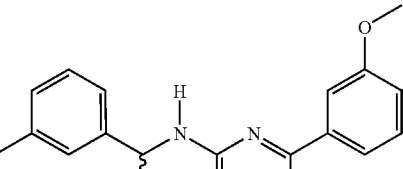<br>C22H25FN4O3S | − | + | + | + | + | NT |
| 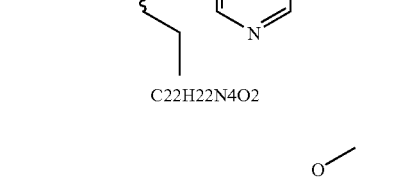<br>C20H22N4O2 | + | + | + | + | + | + |

TABLE 1-continued
| CHEMISTRY | DU145 | PC3 | K562 | TelJak2 | TelJak3 | Tubulin |
|---|---|---|---|---|---|---|
| 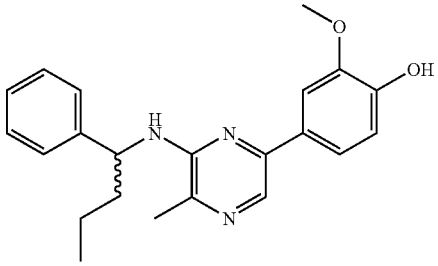 C22H25N3O2 | + | + | + | + | + | + |
| 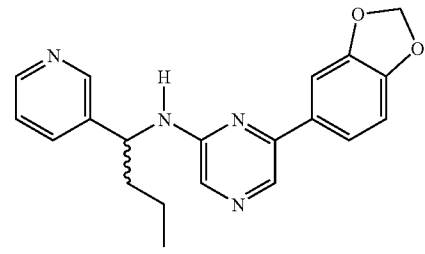 C20H20N4O2 | − | − | + | + | + | NT |
| 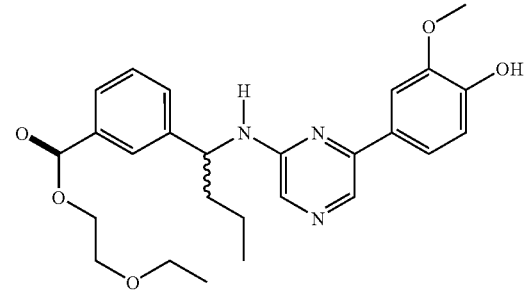 C26H31N3O5 | − | − | + | + | + | NT |
| 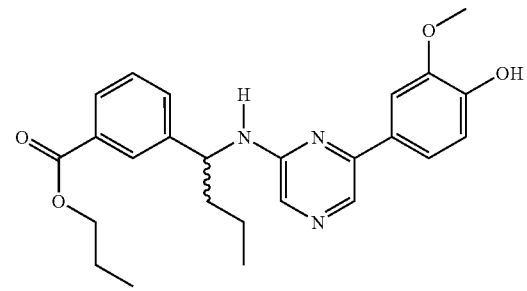 C25H29N3O4 | − | + | + | + | + | NT |
| 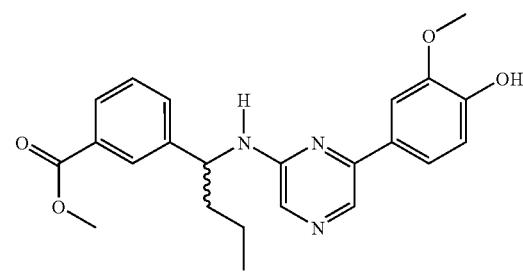 C23H25N3O4 | + | + | + | + | + | + |

TABLE 1-continued
| CHEMISTRY | DU145 | PC3 | K562 | TelJak2 | TelJak3 | Tubulin |
|---|---|---|---|---|---|---|
| 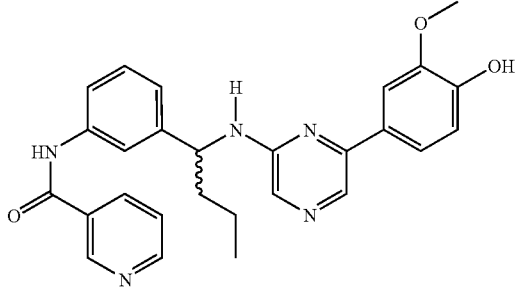 C27H27N5O3 | + | + | + | + | + | + |
| 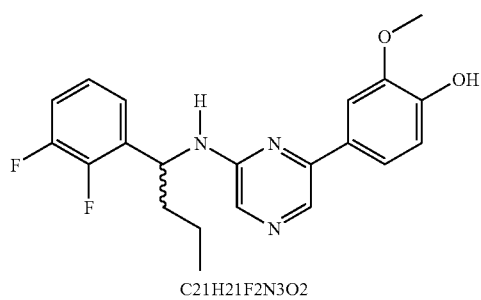 C21H21F2N3O2 | − | − | + | + | + | NT |
| 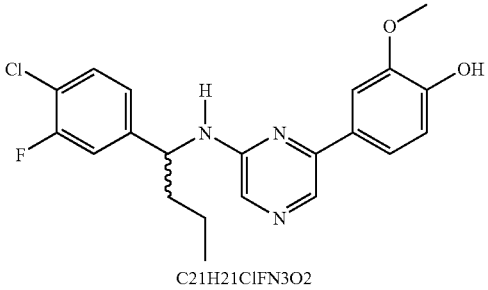 C21H21ClFN3O2 | − | − | + | + | + | NT |
| 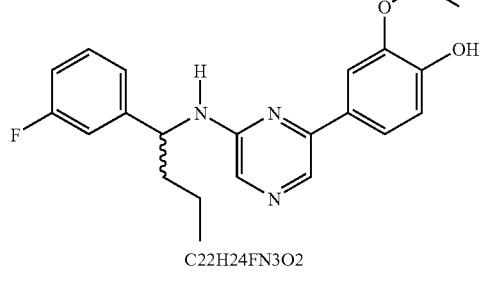 C22H24FN3O2 | − | + | + | + | + | NT |
| 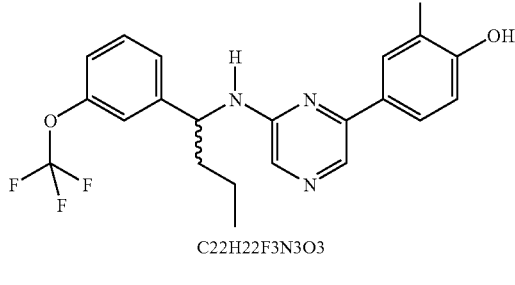 C22H22F3N3O3 | − | − | + | + | + | NT |

TABLE 1-continued
| CHEMISTRY | DU145 | PC3 | K562 | TelJak2 | TelJak3 | Tubulin |
|---|---|---|---|---|---|---|
| 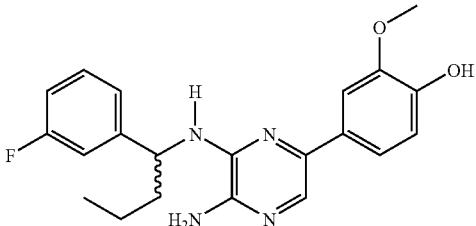<br>C21H23FN4O2 | − | − | + | + | + | NT |
| 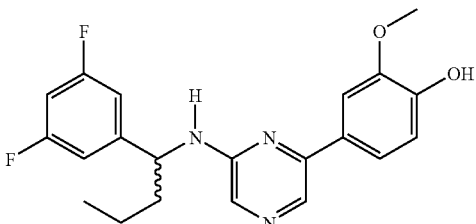<br>C21H21F2N3O2 | − | − | + | + | + | + |
| 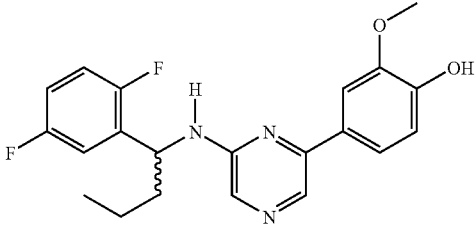<br>C21H21F2N3O2 | − | − | + | + | + | NT |
| 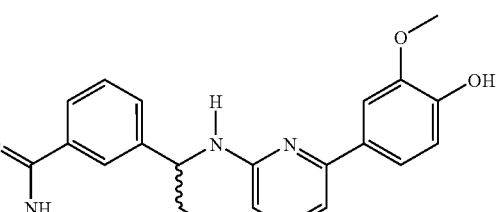<br>C23H26N4O3 | − | − | + | + | + | NT |
| 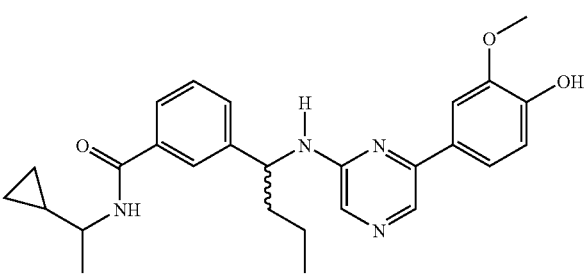<br>C26H30N4O3 | − | − | + | + | + | NT |

TABLE 1-continued
| CHEMISTRY | DU145 | PC3 | K562 | TelJak2 | TelJak3 | Tubulin |
|---|---|---|---|---|---|---|
| 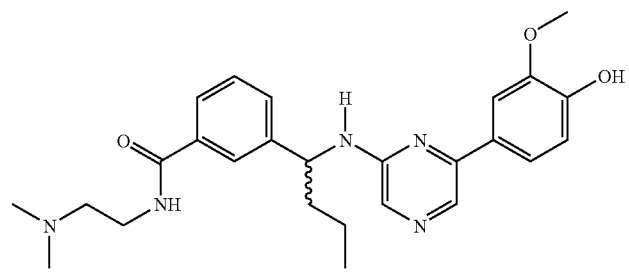 C26H33N5O3 | − | + | + | + | + | NT |
| 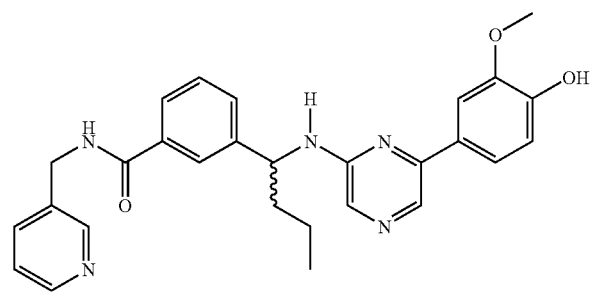 C28H29N5O3 | − | − | + | + | + | NT |
| 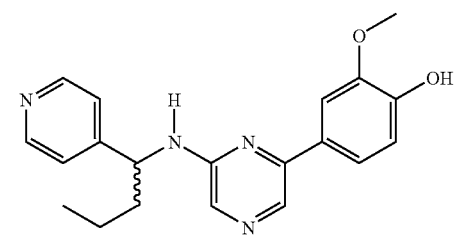 C20H22N4O2 | − | NT | + | + | + | NT |
| 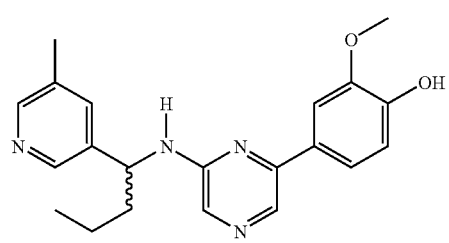 C21H24N4O2 | − | + | + | + | + | + |
| 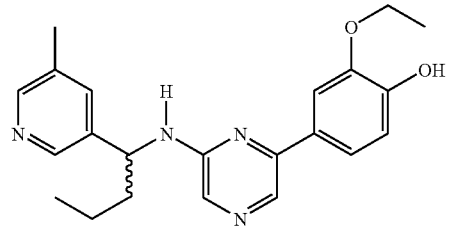 C22H26N4O2 | − | + | + | + | + | NT |

TABLE 1-continued
| CHEMISTRY | DU145 | PC3 | K562 | TelJak2 | TelJak3 | Tubulin |
|---|---|---|---|---|---|---|
| 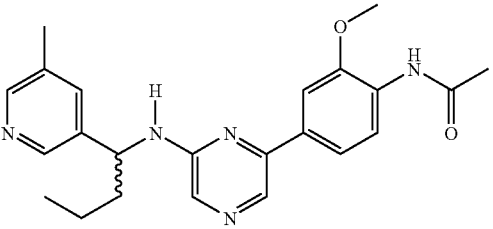 C23H27N5O2 | + | − | + | + | + | NT |
| 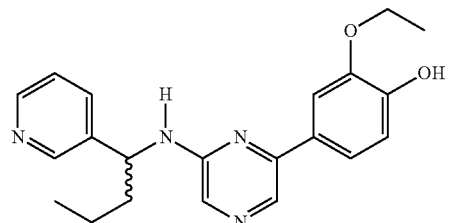 C21H24N4O2 | − | + | + | + | + | NT |
| 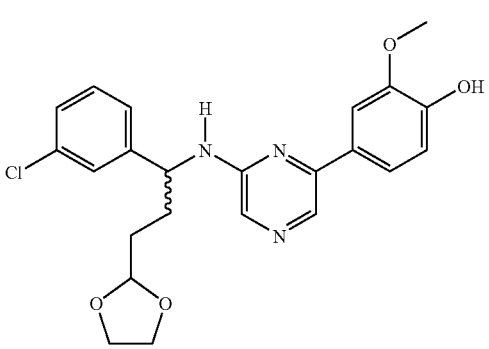 C23H24ClN3O4 | − | − | + | + | + | NT |
| 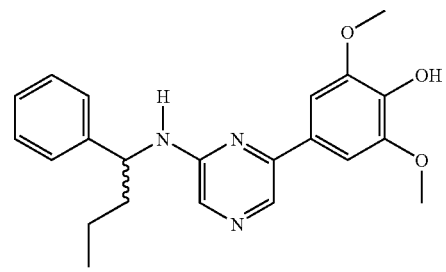 C22H25N3O3 | − | − | − | + | + | NT |
| 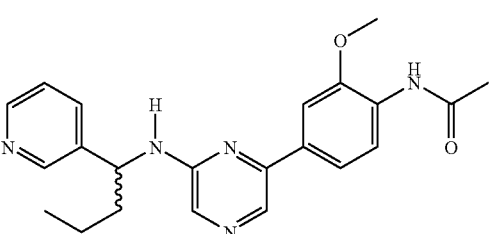 C22H25N5O2 | − | + | + | + | + | NT |

TABLE 1-continued
| CHEMISTRY | DU145 | PC3 | K562 | TelJak2 | TelJak3 | Tubulin |
|---|---|---|---|---|---|---|
| 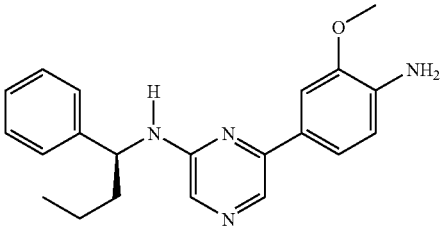<br>C21H24N4O | + | + | + | + | + | + |
| 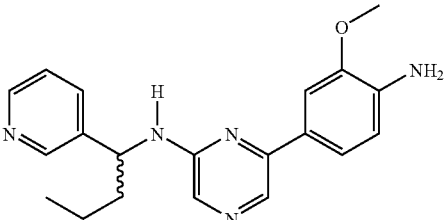<br>C20H23N5O | + | + | + | + | + | + |
| 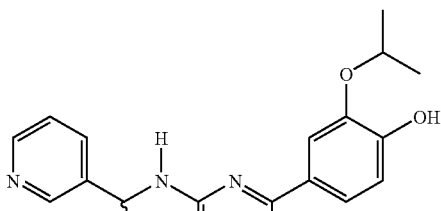<br>C22H26N4O2 | + | + | + | + | + | + |
| 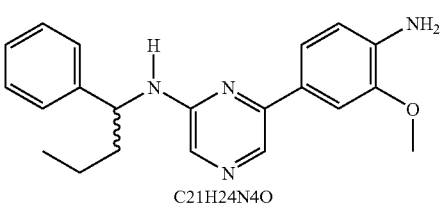<br>C21H24N4O | − | − | + | + | + | NT |
| 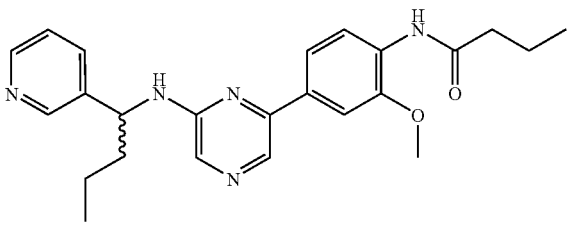<br>C24H29N5O2 | NT | + | + | + | + | NT |
| 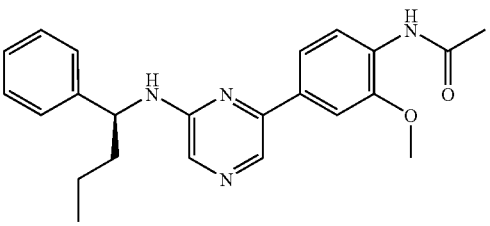<br>C23H26N4O2 | NT | − | NT | + | + | NT |

TABLE 1-continued
| CHEMISTRY | DU145 | PC3 | K562 | TelJak2 | TelJak3 | Tubulin |
|---|---|---|---|---|---|---|
| 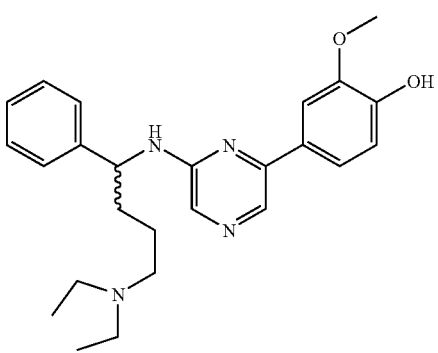 C25H32N4O2 | − | − | − | + | + | NT |
| 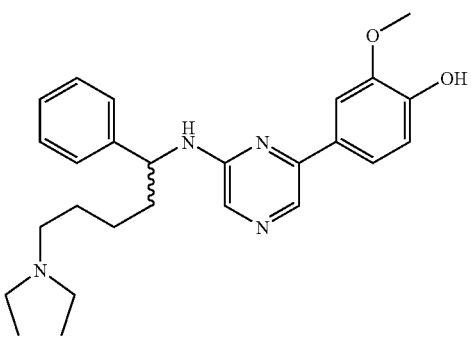 C26H34N4O2 | + | − | − | + | + | NT |
| 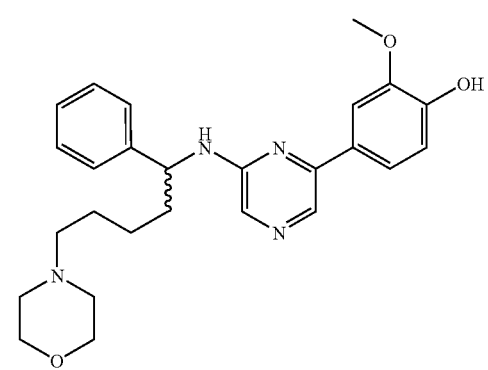 C26H32N4O3 | − | − | − | + | + | NT |
| 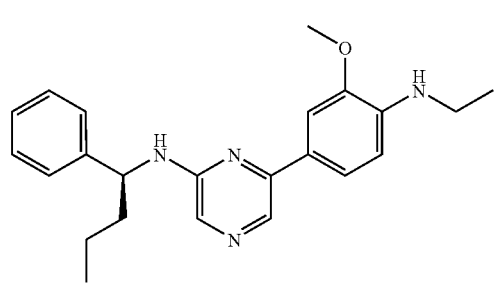 C23H28N4O | − | + | + | + | + | NT |

TABLE 1-continued

| CHEMISTRY | DU145 | PC3 | K562 | TelJak2 | TelJak3 | Tubulin |
|---|---|---|---|---|---|---|
| 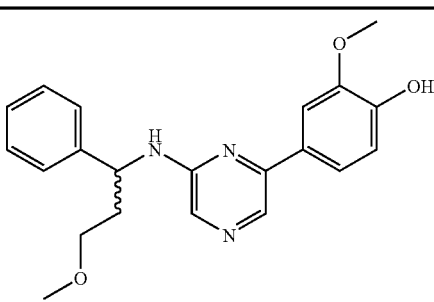 C21H23N3O3 | + | + | + | + | + | + |
| 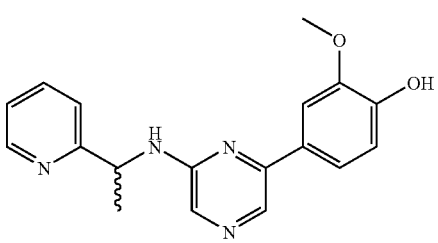 C18H18N4O2 | − | − | − | + | + | NT |
| 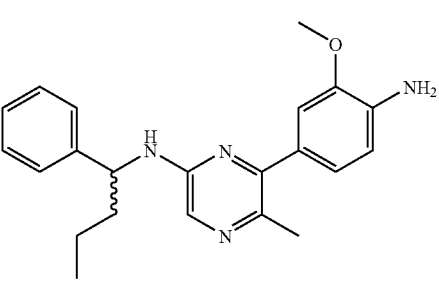 C22H26N4O | + | + | + | + | + | + |
| 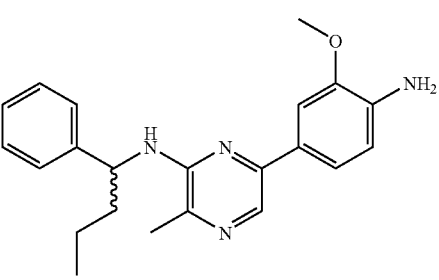 C22H26N4O | + | + | + | + | + | + |
| 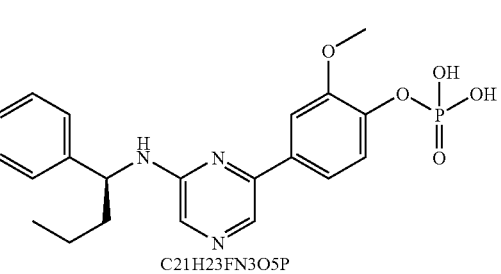 C21H23FN3O5P | + | + | + | + | + | + |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A tubulin inhibitor of the formula I:

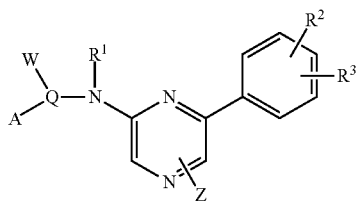

wherein:

R¹ is H, $C_{1-6}$ alkyl, $C_{1-6}$ alkylNR⁵R⁶, $C_{1-6}$ alkylNR⁵COR⁶, $C_{1-6}$ alkylNR⁵SO₂R⁶, $C_{1-6}$ alkylCO₂R⁵, $C_{1-6}$ alkylCONR⁵R⁶, where R⁵ and R⁶ are each independently H, $C_{1-4}$ alkyl, aryl, hetaryl, $C_{1-4}$ alkylaryl, $C_{1-4}$ alkylhetaryl or may be joined to form a 3-8 membered ring optionally containing an atom selected from O, S, NR⁷ and R⁷ is selected from H, $C_{1-4}$ alkyl;

R² and R³ are each independently halogen, $C_{1-4}$ alkyl, OH, $OC_{1-4}$ alkyl, CF₃, OCF₃, CN, $C_{1-4}$ alkylNR⁸R⁹, $OC_{1-4}$ alkylNR⁸R⁹, OCONR⁸R⁹, NR⁸R⁹, NR⁸COR⁹, NR¹⁰CONR⁸R⁹, NR⁸SO₂R⁹, COOR⁸, CONR⁸R⁹; wherein R⁸, R⁹ and R¹⁰ are each independently H, $C_{1-4}$ alkyl, $C_{1-4}$ alkyl cycloalkyl, or may be joined to form a 3-8 membered ring optionally containing an atom selected from O, S, NR¹¹; wherein R¹¹ is H, $C_{1-11}$ alkyl or CF₃;

alternatively, R² and R³, when located on adjacent carbon atoms, may be joined to form the ring system

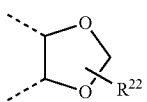

where R²² is H, $C_{1-4}$ alkyl, or CF₃;

Q is $C_{1-4}$ alkylene;

W is $C_{2-4}$alkyl or $C_{2-6}$alkenyl, where $C_{2-4}$alkyl or $C_{2-6}$alkenyl may be optionally substituted with $C_{1-4}$ alkyl, OH, $OC_{1-4}$ alkyl, NR¹⁵R¹⁶; wherein R¹⁵, and R¹⁶ are each independently H, $C_{1-4}$ alkyl, $C_{1-4}$ alkyl cycloalkyl, $C_{1-4}$ alkyl cyclohetalkyl, aryl, hetaryl, or may be joined to form a 3-8 membered ring optionally containing an atom selected from O, S, NR¹⁷ wherein R¹⁷ is H or $C_{1-4}$ alkyl;

A is aryl, or hetaryl each optionally substituted with 0-3 substituents independently selected from halogen, $C_{1-4}$ alkyl, CF₃, aryl, hetaryl, OCF₃, $OC_{1-4}$ alkyl, $OC_{2-5}$ alkylNR¹⁸R¹⁹, Oaryl, Ohetaryl, $CO_2R^{18}$, CONR¹⁸R¹⁹, NR¹⁸R¹⁹, $C_{1-4}$ alkylNR¹⁸R¹⁹, NR²⁰$C_{1-4}$ alkylNR¹⁸R¹⁹, NR¹⁸COR¹⁹, NR²⁰CONR¹⁸R¹⁹, NR¹⁸SO₂R¹⁹; wherein R¹⁸, R¹⁹ are each independently H, $C_{1-4}$ alkyl, $C_{1-4}$ alkyl cyclohetalkyl, aryl, hetaryl, $C_{1-4}$ alkyl aryl, $C_{1-4}$ alkyl hetaryl, or may be joined to form a 3-8 membered ring optionally containing an atom selected from O, S, NR²¹; wherein R²⁰ and R²¹ are independently H or $C_{1-4}$ alkyl; and Z is H or $C_{1-4}$ alkyl, or a tubulin inhibitor of the formula

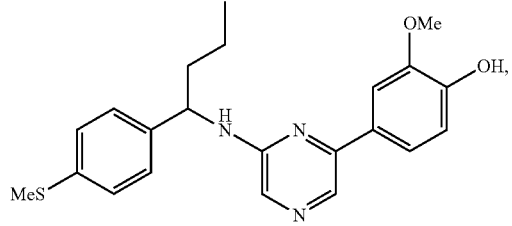

1-1

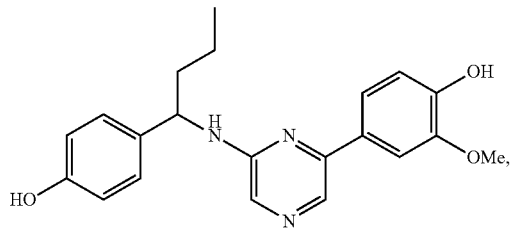

1-2

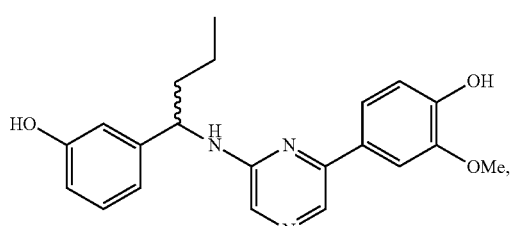

1-3

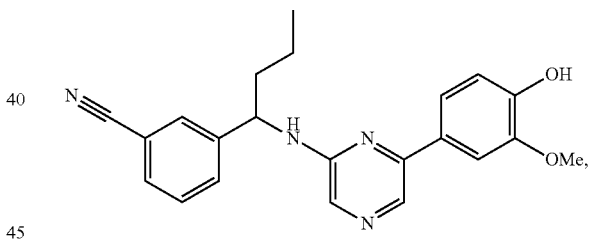

1-4

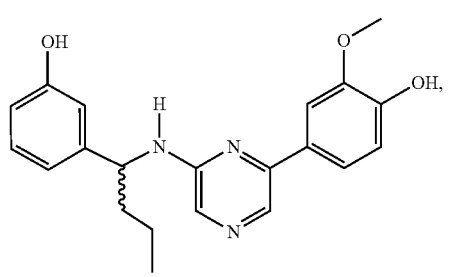

1-5

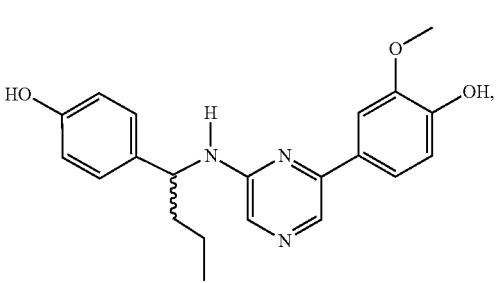

1-6

-continued 1-7

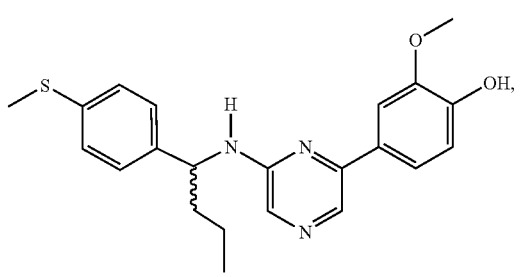

1-8

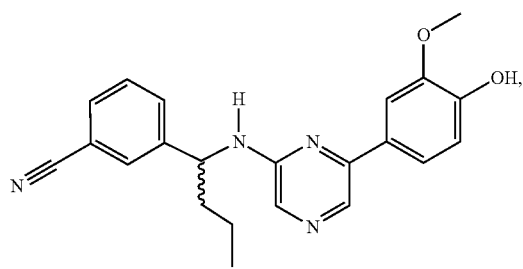

1-9

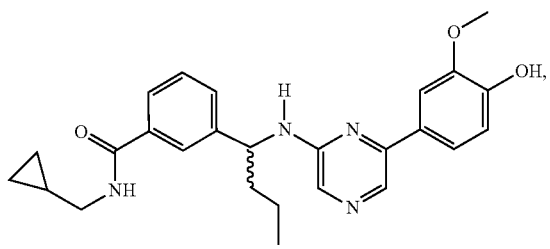

or pharmaceutically acceptable prodrugs, salts or stereoisomers thereof,
wherein prodrugs are esters of a free carboxy or hydroxy group or amides of a free amino group.

2. A tubulin inhibitor according to claim 1 wherein W is $C_{2-4}$alkyl or $C_{2-4}$alkylamino which is a mixture of the compound that possesses S chirality at the chiral carbon bearing W, and the compound that possesses R chirality at said carbon.

3. A tubulin inhibitor according to claim 2 wherein the mixture comprises at least 70% of the compound that possesses S chirality at said carbon.

4. A tubulin inhibitor according to claim 3 wherein the compound comprises at least 80% of the compound that possesses S chirality at said carbon.

5. A tubulin inhibitor according to claim 3 wherein the compound comprises at least 90% of the compound that possesses S chirality at said carbon.

6. A tubulin inhibitor according to claim 3 wherein the compound comprises at least 95% of the compound that possesses S chirality at said carbon.

7. A tubulin inhibitor according to claim 3 wherein the compound comprises at least 99% of the compound that possesses S chirality at said carbon.
and the pharmaceutically acceptable salts and stereoisomers thereof.

8. A composition comprising a carrier and at least one tubulin inhibitor of claim 1.

9. A method of modulating microtubule polymerization in a cell wherein said method comprises administering a tubulin inhibitor according to claim 1.

10. A tubulin inhibitor of the formula II:

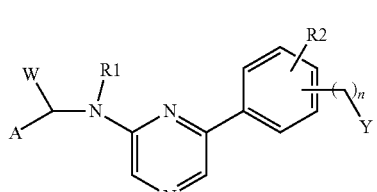

II or pharmaceutically acceptable prodrugs, salts or stereoisomers thereof, wherein:

$R^1$ is H, $C_{1-6}$ alkyl, $C_{1-6}$ alkyl$NR^5R^6$, where $R^5$ and $R^6$ are each independently H or $C_{1-4}$ alkyl, or may be joined to form a 3-8 membered ring optionally containing an atom selected from O, S, $NR^7$ wherein $R^7$ is H or $C_{1-4}$ alkyl;

A is aryl or hetaryl each optionally substituted with 0-3 substituents independently selected from halogen, $C_{1-4}$alkyl, $CF_3$, aryl, hetaryl, $OCF_3$, $OC_{1-4}$alkyl, $OC_{2-5}$alkyl$NR^{18}R^{19}$, Oaryl, Ohetaryl, $CO_2R^{18}$, $CONR^{18}R^{19}$, $NR^{18}R^{19}$, $C_{1-4}$alkyl$NR^{18}R^{19}$, $NR^{20}C_{1-4}$alkyl$NR^{18}R^{19}$, $NR^{18}COR^{19}$, $NR^{20}CONR^{18}R^{19}$, $NR^{18}SO_2R^{19}$, where $R^{18}$ and $R^{19}$ are each independently H, $C_{1-4}$alkyl, $C_{1-4}$alkylcyclohetalkyl, aryl, hetaryl, $C_{1-4}$alkylaryl, $C_{1-4}$alkylhetaryl, or may be joined to form a 3-8 membered ring optionally containing an atom selected from O, S or $NR^{21}$; $R^{20}$ is H or $C_{1-4}$alkyl; wherein $R^{21}$ is H or $C_{1-4}$alkyl;

$R^2$ is 1-2 substituents independently selected from halogen, $C_{1-4}$ alkyl, OH, $OC_{1-4}$ alkyl, $CF_3$, $OCF_3$, CN, $C_{1-4}$alkyl$NR^8R^9$, $OC_{1-4}$ alkyl$NR^8R^9$, $CO_2R^8$, $CONR^8R^9$, $NR^8R^9$, $NR^8COR^9$, $NR^{10}CONR^8R^9$, $NR^8SO_2R^9$; wherein $R^8$, $R^9$ and $R^{10}$ are each independently H or $C_{1-4}$ alkyl;

Y is H, OH, $NR^{12}R^{13}$; and $R^{12}$, wherein $R^{13}$ are each independently H or $C_{1-4}$ alkyl, or may be joined to form a 3-6 membered ring optionally containing an atom selected from O, S, $NR^{14}$ wherein $R^{14}$ is H or $C_{1-4}$ alkyl;

n is 0, 1, 2, 3 or 4;

with the proviso that if $R^2$ represents 2 substituents, n is 0 and Y is H; and if $R^2$ represents one substituent and n is 0, Y cannot be H;

W is $C_{2-4}$alkyl or $C_{2-6}$alkenyl, where $C_{2-4}$alkyl or $C_{2-6}$alkenyl may be optionally substituted with $C_1$-alkyl, OH, $OC_{1-4}$ alkyl or $NR^{15}R^{16}$; wherein $R^{15}$ and $R^{16}$ are each independently H, $C_{1-4}$ alkyl, $C_{1-4}$ alkylcycloalkyl, $C_{1-4}$ alkylcyclohetalkyl, aryl or hetaryl, or may be joined to form a 3-8 membered ring optionally containing an atom selected from O, S or $NR^{17}$; wherein $R^{17}$ is selected from H or $C_{1-4}$alkyl;

wherein prodrugs are esters of a free carboxy or hydroxy group or amides of a free amino group.

11. A composition comprising a carrier and at least one tubulin inhibitor of claim 10.

12. A method of modulating microtubule polymerization in a cell wherein said method comprises administering a tubulin inhibitor according to claim 10.

13. A tubulin inhibitor selected from the group consisting of:
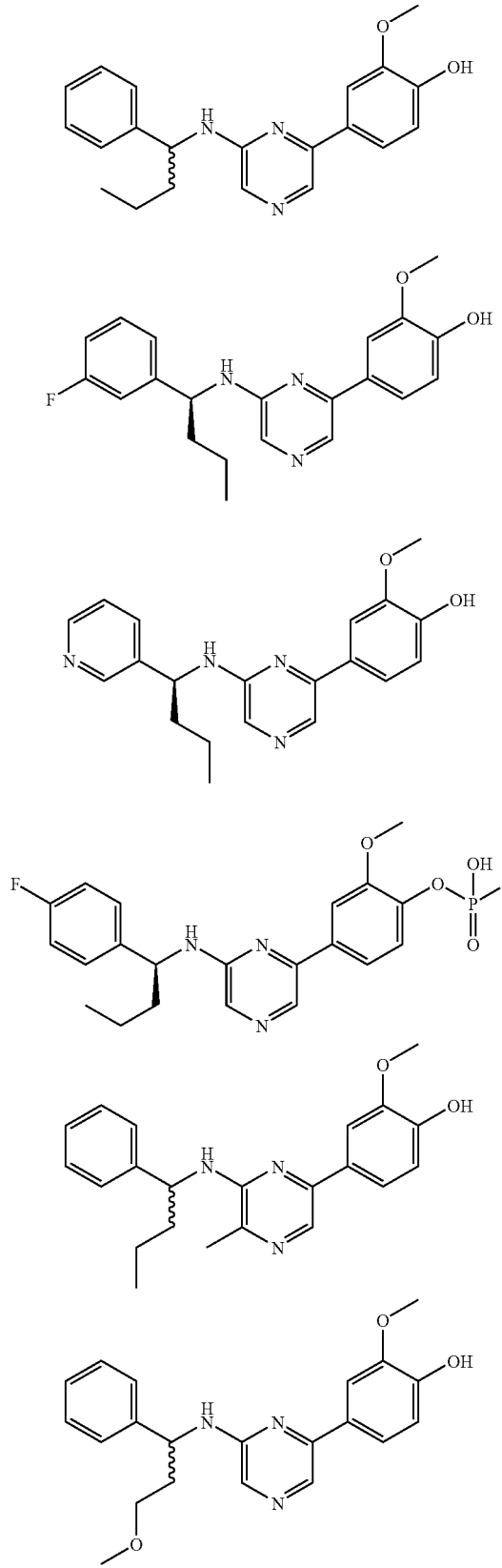
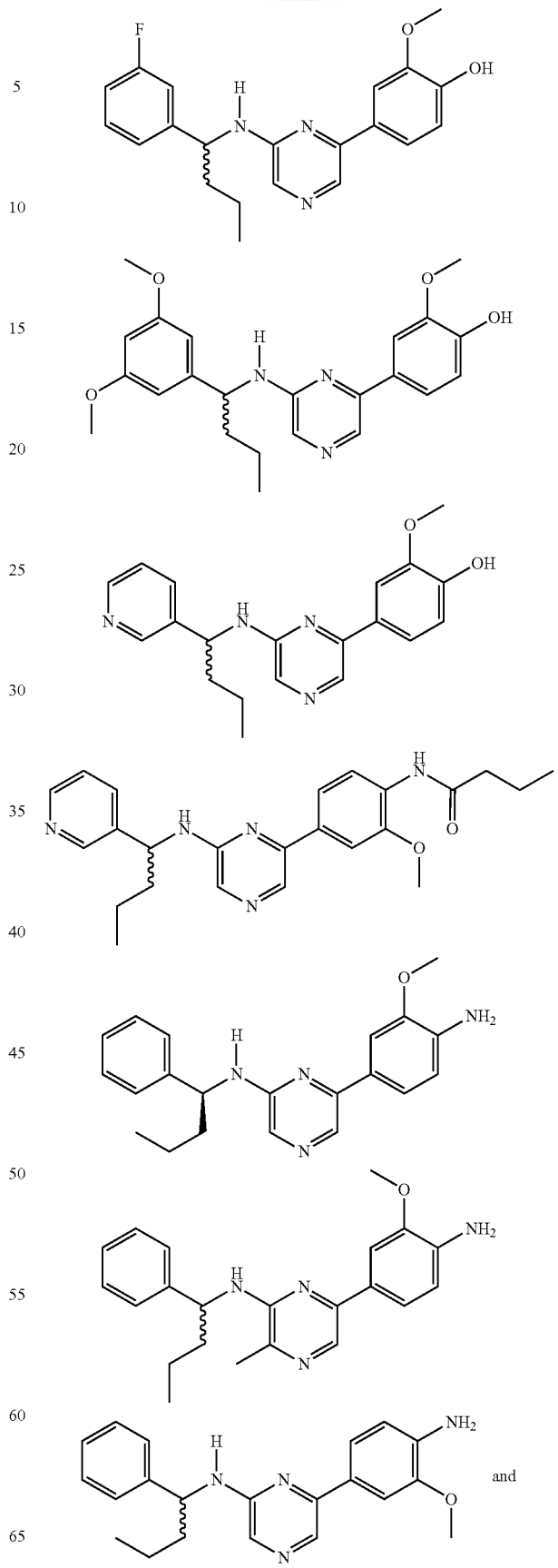
and -continued
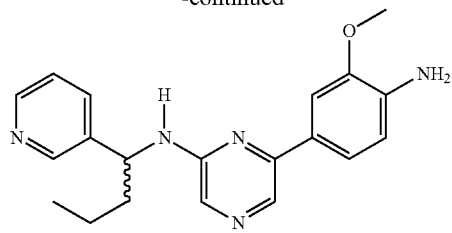
14. A composition comprising a carrier and at least one tubulin inhibitor of claim 13.
15. A method of modulating microtubule polymerization in a cell wherein said method comprises administering a tubulin inhibitor according to claim 13.
* * * * *

SEQUENCE LISTING

<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
ggaggatcct gatctctctc gctgtgagac                               30

<210> SEQ ID NO 2
<211> LENGTH: 28
<212> TYPE: DNA
<213> ORGANISM: Artificial Sequence
<220> FEATURE:
<223> OTHER INFORMATION: Primer

<400> SEQUENCE: 2
aggcgtcgac ttcttcttca tggttctg                                 28

<210> SEQ ID NO 3
<211> LENGTH: 31
<212> TYPE: DNA
<213> ORGANISM: Artificial Sequence
<220> FEATURE:
<223> OTHER INFORMATION: Primer

<400> SEQUENCE: 3
acgcgtcgac ggtgcctttg aagaccggga t                             31

<210> SEQ ID NO 4
<211> LENGTH: 34
<212> TYPE: DNA
<213> ORGANISM: Artificial Sequence
<220> FEATURE:
<223> OTHER INFORMATION: Primer

<400> SEQUENCE: 4
atagtttagc ggccgctcag aatgaaggtc attt                          34

<210> SEQ ID NO 5
<211> LENGTH: 35
<212> TYPE: DNA
<213> ORGANISM: Artificial Sequence
<220> FEATURE:
<223> OTHER INFORMATION: Primer

<400> SEQUENCE: 5
gaagtcgact atgcctgcca agacccacg atctt                          35

<210> SEQ ID NO 6
<211> LENGTH: 36
<212> TYPE: DNA
<213> ORGANISM: Artificial Sequence
<220> FEATURE:
<223> OTHER INFORMATION: Primer

<400> SEQUENCE: 6
ggatctagac tatgaaaagg acagggagtg gtgttt                        36